(12) United States Patent
Villedieu-Percheron et al.

(10) Patent No.: US 9,119,398 B2
(45) Date of Patent: Sep. 1, 2015

(54) PLANT GROWTH REGULATING COMPOUNDS

(71) Applicant: Syngenta Participations AG, Basel (CH)

(72) Inventors: Emmanuelle Villedieu-Percheron, Stein (CH); Didier Zurwerra, Stein (CH); Mathilde Denise Lachia, Stein (CH); Hanno Christian Wolf, Stein (CH); Pierre Joseph Marcel Jung, Stein (CH); Franciscus Lanfermeijer, Enkhuizen (NL); Paul Van Den Wijngaard, Enkhuizen (NL); Claudio Screpanti, Stein (CH); Alain De Mesmaeker, Stein (CH)

(73) Assignee: Syngenta Participations AG, Basel (CH)

( * ) Notice: Subject to any disclaimer, the term of this patent is extended or adjusted under 35 U.S.C. 154(b) by 0 days.

(21) Appl. No.: 14/398,140

(22) PCT Filed: May 7, 2013

(86) PCT No.: PCT/EP2013/059458
§ 371 (c)(1),
(2) Date: Oct. 31, 2014

(87) PCT Pub. No.: WO2013/171092
PCT Pub. Date: Nov. 21, 2013

(65) Prior Publication Data
US 2015/0087508 A1    Mar. 26, 2015

(30) Foreign Application Priority Data

May 14, 2012 (GB) .................................. 1208561.9
Jun. 11, 2012 (GB) .................................. 1210394.1

(51) Int. Cl.
*A01N 43/46* (2006.01)
*A01N 43/38* (2006.01)
*C07D 405/12* (2006.01)
*C07D 407/12* (2006.01)

(52) U.S. Cl.
CPC ................ *A01N 43/46* (2013.01); *A01N 43/38* (2013.01); *C07D 405/12* (2013.01); *C07D 407/12* (2013.01)

(58) Field of Classification Search
CPC .... C07D 407/12; C07D 405/12; A01N 43/38; A01N 43/46
See application file for complete search history.

(56) References Cited

PUBLICATIONS

Johnsson et al., The preparation of synthetic analogues of strigol, Journal of the Chemical Society, 1981, Perkin Transactions 1, Chemical Society, Letchworth, GB, No. 6, p. 1734-1743.
International Search Report and Written Opinion for International Patent Application No. PCT/EP2013/059458 dated Oct. 16, 2013.

*Primary Examiner* — Noble Jarrell
*Assistant Examiner* — John Mauro
(74) *Attorney, Agent, or Firm* — R. Kody Jones

(57) ABSTRACT

The present invention relates to novel strigolactam derivatives, to processes and intermediates for preparing them, to plant growth regulator compositions comprising them and to methods of using them for controlling the growth of plants and/or promoting the germination of seeds.

10 Claims, No Drawings

PLANT GROWTH REGULATING COMPOUNDS

RELATED APPLICATION INFORMATION

This application is a 371 of International Application No. PCT/EP2013/059458, filed 7 May 2013, which claims priority to GB Patent Application No. 1208561.9, filed on 14 May 2012, and GB Patent Application No. 1210394.1, filed on 11 Jun. 2012, the contents of which are incorporated herein by reference.

The present invention relates to novel strigolactam derivatives, to processes and intermediates for preparing them, to plant growth regulator compositions comprising them and to methods of using them for controlling the growth of plants and/or promoting the germination of seeds.

Strigolactone derivatives are phytohormones with plant growth regulation and seed germination properties; they have been described, for example, in WO2009/138655, WO2010/125065, WO05/077177, WO06/098626, WO11/125,714 and Annual Review of Phytopathology (2010), 48 p. 93-117. Strigolactone derivatives, like the synthetic analogue GR24, are known to have effect on the germination of parasitic weeds, such as *Orobanche* species. It is well established in the art that testing for germination of *Orobanche* seeds is a useful test to identify strigolactone analogues (for example, see Plant and Cell Physiology (2010), 51(7) p. 1095; and Organic & Biomolecular Chemistry (2009), 7(17), p. 3413).

It has now surprisingly been found that certain strigolactam derivatives have properties analogous to strigolactone.

According to the present invention, there is provided a compound of Formula (I)

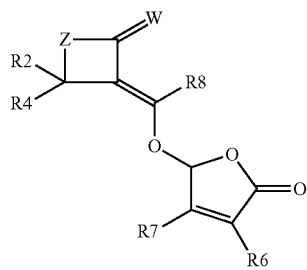

wherein
W is O or S;
Z is NR1, C(R3R5)NR1, C(R11R12)C(R3R5)NR1, C(R13R14)C(R11R12)C(R3R5)NR1, provided that NR1 is always in alpha of the C=W group;
R1 is hydrogen, $C_1$-$C_6$ alkoxy, hydroxyl, amine, N—$C_1$-$C_6$ alkyl amine, N,N-di-$C_1$-$C_6$ alkyl amine, $C_1$-$C_6$ alkyl optionally substituted by one to five R10, $C_1$-$C_6$ haloalkoxy, $C_1$-$C_8$ alkylcarbonyl, $C_1$-$C_8$ alkoxycarbonyl, $C_1$-$C_8$ alkylsulfonyl, $C_1$-$C_6$ alkylsulfinyl, aryl optionally substituted by one to five R10, heteroaryl optionally substituted by one to five R10, heterocyclyl optionally substituted by one to five R10, or benzyl optionally substituted by one to five R10;
R2, R3, R4, R5, R11, R12, R13 and R14 are independently selected from the group consisting of:
(i) A bond, hydrogen, halogen, hydroxyl, nitro, cyano, formyl, formyloxo, formylamino, acetyloxo, $C_1$-$C_6$ alkoxy, $C_1$-$C_6$ haloalkoxy, $C_1$-$C_6$ alkyl optionally substituted by one to five R10, $C_1$-$C_6$ alkylcarbonyl, $C_1$-$C_6$ alkoxycarbonyl, hydroxycarbonyl, aminocarbonyl, N—$C_1$-$C_6$ alkyl amine, N,N-di-$C_1$-$C_6$ alkyl amine, $C_1$-$C_6$ alkylthio, $C_1$-$C_6$haloalkylthio, $C_1$-$C_6$ alkylsulfinyl, $C_1$-$C_6$ haloalkylsulfinyl, $C_1$-$C_8$ alkylsulfonyl, $C_1$-$C_6$ haloalkylsulfonyl, aryl optionally substituted by one to five R10, heteroaryl optionally substituted by one to five R10, vinyl optionally substituted by one to three R9, ethynyl optionally substituted by one R9, a saturated or partially unsaturated 3 to 7 membered cycloalkyl or heterocyclyl, optionally substituted by R10;
(ii) Any two of R2, R3, R4, R5, R11, R12, R13 and R14 can form a saturated or partially unsaturated 3 to 7 membered cycloalkyl or heterocyclyl, optionally substituted by R9; and
(iii) R2 and R4, R3 and R5, R11 and R12 and/or R13 and R14 form an oxo group;
R6 and R7 are independently hydrogen, $C_1$-$C_3$ alkyl, hydroxyl, halogen or $C_1$-$C_3$ alkoxy;
R8 is hydrogen, $C_1$-$C_6$ alkyl optionally substituted by one to five R10, halogen, $C_1$-$C_6$ alkylthio, $C_1$-$C_6$haloalkylthio, $C_1$-$C_6$ alkylsulfinyl, N—$C_1$-$C_6$ alkyl amine, N,N-di-$C_1$-$C_6$ alkyl amine, $C_1$-$C_6$ haloalkylsulfinyl, $C_1$-$C_6$ alkylsulfonyl, or $C_1$-$C_6$ haloalkylsulfonyl;
R9 is halogen, cyano, nitro, $C_1$-$C_6$ alkyl, $C_1$-$C_6$ haloalkyl, $C_1$-$C_6$ haloalkoxy, $C_1$-$C_6$ alkoxy, acetyloxo, amine, N—$C_1$-$C_6$ alkyl amine, N,N-di-$C_1$-$C_6$ alkyl amine, $C_1$-$C_6$ alkyl optionally substituted by one to five R10, $C_1$-$C_6$ alkylcarbonyl, $C_1$-$C_6$ alkoxycarbonyl, aryl optionally substituted by one to five R10, $C_2$-$C_6$ alkenyl, or $C_2$-$C_6$ alkynyl, $C_1$-$C_6$ alkylthio, $C_1$-$C_8$ haloalkylthio, $C_1$-$C_6$ alkylsulfinyl, $C_1$-$C_6$ haloalkylsulfinyl, $C_1$-$C_6$ alkylsulfonyl, or $C_1$-$C_6$ haloalkylsulfonyl;
R10 is hydroxyl, acetyloxo, cyano, nitro, halogen, $C_1$-$C_6$ alkyl, $C_1$-$C_6$ alkoxy, $C_1$-$C_6$ haloalkoxy, $C_1$-$C_6$ haloalkyl, $C_2$-$C_6$ alkenyl, or $C_2$-$C_6$ alkynyl, $C_1$-$C_6$ alkylthio, $C_1$-$C_8$ haloalkylthio, $C_1$-$C_6$ alkylsulfinyl, N—$C_1$-$C_6$ alkyl amine, N,N-di-$C_1$-$C_6$ alkyl amine, $C_1$-$C_8$ haloalkylsulfinyl, $C_1$-$C_8$ alkylsulfonyl, or $C_1$-$C_8$haloalkylsulfonyl;
or salts or N-oxides thereof.

The compounds of Formula (I) may exist in different geometric or optical isomers (diastereoisomers and enantiomers) or tautomeric forms. This invention covers all such isomers and tautomers and mixtures thereof in all proportions as well as isotopic forms such as deuterated compounds. The invention also covers all salts, N-oxides, and metalloidic complexes of the compounds of Formula (I).

Each alkyl moiety either alone or as part of a larger group (such as alkoxy, alkoxycarbonyl, alkylcarbonyl, alkylaminocarbonyl, dialkylaminocarbonyl) is a straight or branched chain and is, for example, methyl, ethyl, n-propyl, n-butyl, n-pentyl, n-hexyl, iso-propyl, n-butyl, sec-butyl, iso-butyl, tert-butyl or neo-pentyl. The alkyl groups are preferably $C_1$ to $C_6$ alkyl groups, more preferably $C_1$-$C_4$ and most preferably $C_1$-$C_3$ alkyl groups.

Halogen is fluorine, chlorine, bromine or iodine.

Haloalkyl groups (either alone or as part of a larger group, such as haloalkoxy or haloalkylthio) are alkyl groups which are substituted with one or more of the same or different halogen atoms and are, for example, —$CF_3$, —$CF_2Cl$, —$CH_2CF_3$ or —$CH_2CHF_2$.

Hydroxyalkyl groups are alkyl groups which are substituted with one or more hydroxyl group and are, for example, —$CH_2OH$, —$CH_2CH_2OH$ or —$CH(OH)CH_3$.

In the context of the present specification the term "aryl" refers to a ring system which may be mono-, bi- or tricyclic. Examples of such rings include phenyl, naphthalenyl, anthracenyl, indenyl or phenanthrenyl. A preferred aryl group is phenyl.

Unless otherwise indicated, alkenyl and alkynyl, on their own or as part of another substituent, may be straight or branched chain and may preferably contain 2 to 6 carbon atoms, preferably 2 to 4, more preferably 2 to 3, and where appropriate, may be in either the (E)- or (Z)-configuration. Examples include vinyl, allyl and propargyl.

Unless otherwise indicated, cycloalkyl may be mono- or bi-cyclic, may be optionally substituted by one or more $C_1$-$C_6$ alkyl groups, and preferably contain 3 to 7 carbon atoms, more preferably 3 to 6 carbon atoms. Examples of cycloalkyl include cyclopropyl, 1-methylcyclopropyl, 2-methylcyclopropyl, cyclobutyl, cyclopentyl and cyclohexyl.

The term "heteroaryl" refers to an aromatic ring system containing at least one heteroatom and consisting either of a single ring or of two or more fused rings. Preferably, single rings will contain up to three and bicyclic systems up to four heteroatoms which will preferably be chosen from nitrogen, oxygen and sulfur. Examples of such groups include pyridyl, pyridazinyl, pyrimidinyl, pyrazinyl, furanyl, thiophenyl, oxazolyl, isoxazolyl, oxadiazolyl, thiazolyl, isothiazolyl, thiadiazolyl, pyrrolyl, pyrazolyl, imidazolyl, triazolyl and tetrazolyl. A preferred heteroaryl group is pyridine.

The term "heterocyclyl" is defined to include heteroaryl, saturated analogs, and in addition their unsaturated or partially unsaturated analogues such as 4,5,6,7-tetrahydro-benzothiophenyl, 9H-fluorenyl, 3,4-dihydro-2H-benzo-1,4-dioxepinyl, 2,3-dihydro-benzo-furanyl, piperidinyl, 1,3-dioxolanyl, 1,3-dioxanyl, 4,5-dihydro-isoxazolyl, tetrahydrofuranyl and morpholinyl. In addition, the term "heterocyclyl" is defined to include "heterocycloalkyl" defined to be a non-aromatic monocyclic or polycyclic ring comprising carbon and hydrogen atoms and at least one heteroatom, preferably, 1 to 4 heteroatoms selected from nitrogen, oxygen, and sulfur such as oxirane or thietane.

Preferred values of W, Z, R1, R2, R3, R4, R5, R6, R7, R8, R10, R11, R12, R13 and R14 are, in any combination, as set out below:

W is preferably oxygen.
Z is preferably NR1, C(R3R5)NR1 or C(R11R12)C(R3R5) NR1 provided that NR1 is always in alpha of the C=W group; more preferably Z is C(R3R5)NR1.
R1 is preferably selected from the group consisting of hydrogen, $C_1$-$C_6$ alkoxy, $C_1$-$C_6$ alkyl optionally substituted by one to five R10, $C_1$-$C_8$ alkylcarbonyl, $C_1$-$C_8$ alkoxycarbonyl, aryl optionally substituted by one to five R10, heteroaryl optionally substituted by one to five R10, heterocyclyl optionally substituted by one to five R10, and benzyl optionally substituted by one to five R10. More preferably R1 is selected from the group consisting of hydrogen, $C_1$-$C_6$ alkoxy, $C_1$-$C_6$ alkyl optionally substituted by one to five R10, $C_1$-$C_8$ alkylcarbonyl, $C_1$-$C_8$ alkoxycarbonyl, aryl optionally substituted by one to five R10, and benzyl optionally substituted by one to five R10. More preferably R1 is hydrogen, methyl, ethyl, phenyl, benzyl, acetate, tert-butoxycarbonyl or methoxycarbonyl. In one embodiment, R1 is hydrogen or tert-butoxycarbonyl.
Preferably R2, R3, R4, R5, R11, R12, R13 or R14 are independently selected from the group consisting of:
(i) A bond, hydrogen, $C_1$-$C_6$ alkoxy, $C_1$-$C_6$ alkyl, $C_1$-$C_6$ alkyl optionally substituted by one to five R10, $C_1$-$C_6$ alkoxycarbonyl, aryl optionally substituted by one to five R10, heteroaryl optionally substituted by one to five R10, or saturated or partially unsaturated 3 to 7 membered cycloalkyl or heterocyclyl optionally substituted by R10. More preferably R2, R3, R4, R5, R11, R12, R13 or R14 are independently hydrogen, methyl, ethyl, phenyl;

(ii) Any two of R2, R3, R4, R5, R11, R12, R13 and R14 can form a saturated or partially unsaturated 5 to 6 membered cycloalkyl or heterocyclyl, optionally substituted by R9; and
(iii) R2 and R4, R3 and R5, R11 and R12, and/or R13 and R14 form an oxo group.

More preferably R2, R3, R4, R5, R11, R12, R13 or R14 are independently selected from the group consisting of:
(i) hydrogen, methyl, ethyl, phenyl;
(ii) R2 and R5 or R5 and R11 form a saturated or partially unsaturated 5 to 6 membered cycloalkyl; and
(iii) R2 and R4 and/or R3 and R5 form an oxo group.

R6 is preferably hydrogen, methyl, or ethyl; more preferably R6 is methyl.
R7 is preferably hydrogen, methyl, methoxy, chlorine or ethyl; more preferably R7 is hydrogen.
R8 is preferably hydrogen, methyl, or ethyl; more preferably R8 is hydrogen.
R10 is preferably selected from the group consisting of hydroxyl, cyano, nitro, halogen, $C_1$-$C_6$ alkyl, $C_1$-$C_6$ alkoxy, and $C_1$-$C_6$ haloalkyl; more preferably R10 is cyano, nitro, chlorine, bromine, fluorine, methyl, methoxy, or trifluoromethyl.

In one embodiment of the present invention, there is provided a compound of Formula (I) wherein:
Z is NR1, C(R3R5)NR1, C(R11R12)C(R3R5)NR1 or C(R13R14)C(R11R12) C(R3R5)NR1, provided that NR1 is always in alpha of the C=W group;
W is oxygen;
R1 is hydrogen, $C_1$-$C_6$ alkoxy, $C_1$-$C_6$ alkyl optionally substituted by one to five R10, $C_1$-$C_8$ alkylcarbonyl, $C_1$-$C_8$ alkoxycarbonyl, aryl optionally substituted by one to five R10, heteroaryl optionally substituted by one to five R10, heterocyclyl optionally substituted by one to five R10, or benzyl optionally substituted by one to five R10;
R2, R3, R4, R5, R11, R12, R13 or R14 are independently selected from the group consisting of:
(i) hydrogen, $C_1$-$C_6$ alkoxy, $C_1$-$C_6$ alkyl, $C_1$-$C_6$ alkyl optionally substituted by one to five R10, $C_1$-$C_6$ alkoxycarbonyl, aryl optionally substituted by one to five R10, heteroaryl optionally substituted by one to five R10, or saturated or partially unsaturated 3 to 7 membered cycloalkyl or heterocyclyl optionally substituted by R10;
(ii) Any two of R2, R3, R4, R5, R11, R12, R13 and R14 can form a saturated or partially unsaturated 3 to 7 membered cycloalkyl or heterocyclyl, optionally substituted by R9; and
(iii) R2 and R4, R3 and R5 form an oxo group;
R6 is hydrogen, methyl, or ethyl;
R7 is hydrogen, methyl, methoxy, chlorine or ethyl;
R8 is hydrogen, methyl, or ethyl; and
R10 is hydroxyl, cyano, nitro, halogen, $C_1$-$C_6$ alkyl, $C_1$-$C_6$ alkoxy, or $C_1$-$C_6$ haloalkyl.

In a further embodiment, of the present invention, there is provided a compound of Formula (I) wherein:
Z is NR1, C(R3R5)NR1, C(R11R12)C(R3R5)NR1 or C(R13R14)C(R11R12) C(R3R5)NR1, provided that NR1 is always in alpha of the C=W group;
W is oxygen;
R1 is hydrogen, methyl, ethyl, phenyl, benzyl, acetate, tert-butoxycarbonyl or methoxycarbonyl;
R2, R3, R4, R5, R11, R12, R13 or R14 are independently selected from the group consisting of:
(iv) hydrogen, methyl, ethyl, phenyl;
(v) R2 and R5, or R5 and R11 form a saturated or partially unsaturated 5 to 6 membered cycloalkyl; and
(vi) R2 and R4, and/or R3 and R5 form an oxo group;
R6 is methyl:
R7 is hydrogen;

R8 is hydrogen; and
R10 is cyano, nitro, chlorine, bromine, fluorine, methyl, methoxy, or trifluoromethyl.

In a further embodiment of the present invention, there is provided a compound of Formula (I) wherein:
Z is C(R3R5)NR1 or C(R11R12)C(R3R5)NR1, provided that NR1 is always in alpha of the C=W group;
W is oxygen;
R1 is hydrogen, $C_1$-$C_6$ alkoxy, $C_1$-$C_6$ alkyl optionally substituted by one to five R10, $C_1$-$C_8$ alkylcarbonyl, $C_1$-$C_8$ alkoxycarbonyl, aryl optionally substituted by one to five R10, heteroaryl optionally substituted by one to five R10, heterocyclyl optionally substituted by one to five R10, or benzyl optionally substituted by one to five R10;
R2, R3, R4, R5, R11 or R12 are independently selected from the group consisting of:
(iv) hydrogen, $C_1$-$C_6$ alkoxy, $C_1$-$C_6$ alkyl, $C_1$-$C_6$ alkyl optionally substituted by one to five R10, $C_1$-$C_6$ alkoxycarbonyl, aryl optionally substituted by one to five R10, heteroaryl optionally substituted by one to five R10, or saturated or partially unsaturated 3 to 7 membered cycloalkyl or heterocyclyl optionally substituted by R10;
(v) Any two of R2, R3, R4, R5, R11 and R12 can form a saturated or partially unsaturated 3 to 7 membered cycloalkyl or heterocyclyl, optionally substituted by R9; and
(vi) R2 and R4, R3 and R5, R11 and R12 form an oxo group;
R6 is hydrogen, methyl, or ethyl;
R7 is hydrogen, methyl, methoxy, chlorine or ethyl;
R8 is hydrogen, methyl, or ethyl; and
R10 is hydroxyl, cyano, nitro, halogen, $C_1$-$C_6$ alkyl, $C_1$-$C_6$ alkoxy, or $C_1$-$C_6$ haloalkyl.

In a further embodiment of the present invention, there is provided a compound of Formula (I) wherein:
Z is C(R3R5)NR1 or C(R11R12)C(R3R5)NR1, provided that NR1 is always in alpha of the C=W group;
W is oxygen;
R1 is hydrogen, methyl, ethyl, phenyl, benzyl, acetate, tert-butoxycarbonyl or methoxycarbonyl;
R2, R3, R4, R5, R11 or R12 are independently selected from the group consisting of:
(vii) hydrogen, methyl, ethyl, phenyl;
(viii) R2 and R5, or R5 and R11 form a saturated or partially unsaturated 5 to 6 membered cycloalkyl; and
(ix) R2 and R4 and/or R3 and R5 form an oxo group;
R6 is methyl;
R7 is hydrogen;
R8 is hydrogen; and
R10 is cyano, nitro, chlorine, bromine, fluorine, methyl, methoxy, or trifluoromethyl.

In a preferred embodiment the compound is of Formula (II).

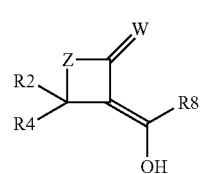

wherein
W is O or S;
with the following paragraph clause:

In a preferred embodiment the compound is of Formula (II).

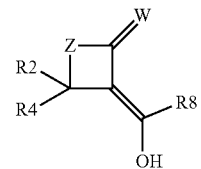

wherein
W is O or S;
Z is NR1, C(R3R5)NR1, C(R11R12)C(R3R5)NR1, C(R13R14)C(R11R12)C(R3R5)NR1, provided that NR1 is always in alpha of the C=W group;
R1 is hydrogen, $C_1$-$C_6$ alkoxy, hydroxyl, amine, N—$C_1$-$C_6$ alkyl amine, N,N-di-$C_1$-$C_6$ alkyl amine, $C_1$-$C_6$ alkyl optionally substituted by one to five R10, $C_1$-$C_6$ haloalkoxy, $C_1$-$C_8$ alkylcarbonyl, $C_1$-$C_8$ alkoxycarbonyl, $C_1$-$C_8$ alkylsulfonyl, $C_1$-$C_6$ alkylsulfinyl, aryl optionally substituted by one to five R10, heteroaryl optionally substituted by one to five R10, heterocyclyl optionally substituted by one to five R10, or benzyl optionally substituted by one to five R10;
R2, R3, R4, R5, R11, R12, R13 and R14 are independently selected from the group consisting of:
(i) A bond, hydrogen, halogen, hydroxyl, nitro, cyano, formyl, formyloxo, formylamino, acetyloxo, $C_1$-$C_6$ alkoxy, $C_1$-$C_6$ haloalkoxy, $C_1$-$C_6$ alkyl optionally substituted by one to five R10, $C_1$-$C_6$ alkylcarbonyl, $C_1$-$C_6$ alkoxycarbonyl, hydroxycarbonyl, aminocarbonyl, N—$C_1$-$C_6$ alkyl amine, N,N-di-$C_1$-$C_6$ alkyl amine, $C_1$-$C_6$ alkylthio, $C_1$-$C_6$haloalkylthio, $C_1$-$C_6$ alkylsulfinyl, $C_1$-$C_6$ haloalkylsulfinyl, $C_1$-$C_8$ alkylsulfonyl, $C_1$-$C_6$ haloalkylsulfonyl, aryl optionally substituted by one to five R10, heteroaryl optionally substituted by one to five R10, vinyl optionally substituted by one to three R9, ethynyl optionally substituted by one R9, a saturated or partially unsaturated 3 to 7 membered cycloalkyl or heterocyclyl, optionally substituted by R10;
(ii) Any two of R2, R3, R4, R5, R11, R12, R13 and R14 can form a saturated or partially unsaturated 3 to 7 membered cycloalkyl or heterocyclyl, optionally substituted by R9; and
(iii) R2 and R4, R3 and R5, R11 and R12 and/or R13 and R14 form an oxo group;
R9 is halogen, cyano, nitro, $C_1$-$C_6$ alkyl, $C_1$-$C_6$ haloalkyl, $C_1$-$C_6$ haloalkoxy, $C_1$-$C_6$ alkoxy, acetyloxo, amine, N—$C_1$-$C_6$ alkyl amine, N,N-di-$C_1$-$C_6$ alkyl amine, $C_1$-$C_6$ alkyl optionally substituted by one to five R10, $C_1$-$C_6$ alkylcarbonyl, $C_1$-$C_6$ alkoxycarbonyl, aryl optionally substituted by one to five R10, $C_2$-$C_6$ alkenyl, or $C_2$-$C_6$ alkynyl, $C_1$-$C_6$ alkylthio, $C_1$-$C_8$ haloalkylthio, $C_1$-$C_6$ alkylsulfinyl, $C_1$-$C_6$ haloalkylsulfinyl, $C_1$-$C_6$alkylsulfonyl, or $C_1$-$C_6$ haloalkylsulfonyl;
R10 is hydroxyl, acetyloxo, cyano, nitro, halogen, $C_1$-$C_6$ alkyl, $C_1$-$C_6$ alkoxy, $C_1$-$C_6$ haloalkoxy, $C_1$-$C_6$ haloalkyl, $C_2$-$C_6$ alkenyl, or $C_2$-$C_6$ alkynyl, $C_1$-$C_6$ alkylthio, $C_1$-$C_8$ haloalkylthio, $C_1$-$C_6$ alkylsulfinyl, N—$C_1$-$C_6$ alkyl amine, N,N-di-$C_1$-$C_6$ alkyl amine, $C_1$-$C_8$ haloalkylsulfinyl, $C_1$-$C_8$ alkylsulfonyl, or $C_1$-$C_8$ haloalkylsulfonyl;
or salts or N-oxides thereof.

The compounds of Formula (II) may exist in different geometric or optical isomers (diastereoisomers and enantiomers) or tautomeric forms. This invention covers all such isomers and tautomers and mixtures thereof in all proportions as well as isotopic forms such as deuterated compounds. The invention also covers all salts, N-oxides, and metalloidic complexes of the compounds of Formula (II).

Preferred values of W, Z, R1, R2, R3, R4, R5, R10, R11, R12, R13 are the same as the preferences set out for the corresponding substituents of the compounds of the Formula (I).

Tables 1 and 2 below include examples of compounds of Formula (I) wherein W is O, R6 is methyl, R8 is H, Z, R1, R2, R3, R4 and R5 are as defined.

TABLE 1

Z = C(R3R5)NR1

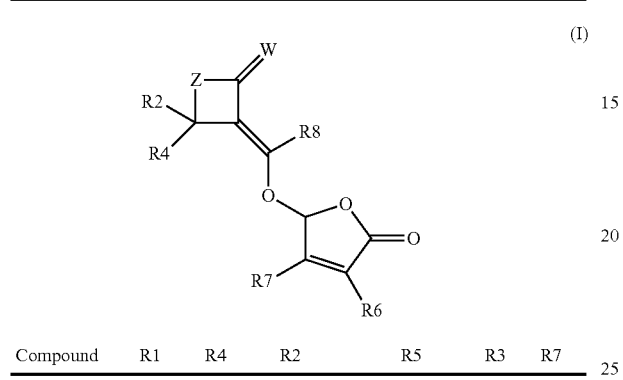

(I)

| Compound | R1 | R4 | R2 | R5 | R3 | R7 |
|---|---|---|---|---|---|---|
| 1.00 | H | H | —CH₂— | | H | H |
| 1.01 | H | H | —CH₂—CH₂—CH₂— | | H | H |
| 1.02 | H | H | —CH=CH—CH₂— | | H | H |
| 1.03 | H | H | —CH₂—CH=CH— | | H | H |
| 1.04 | H | H | —CH₂—CH₂—CH₂—CH₂— | | H | H |
| 1.05 | H | H | —CH=CH—CH₂—CH₂— | | H | H |
| 1.06 | H | H | —CH₂—CH=CH—CH₂— | | H | H |
| 1.07 | H | H | —CH₂—CH₂—CH=CH— | | H | H |
| 1.08 | H | H | H | Ph | H | H |
| 1.09 | H | H | H | cyclopropyl | H | H |
| 1.10 | H | H | cyclopropyl | H | H | H |
| 1.11 | H | H | H | CH₃ | H | H |
| 1.12 | H | H | CH₃ | H | H | H |
| 1.13 | H | H | H | H | H | H |
| 1.14 | H | | O | H | H | H |
| 1.15 | H | | O | CH₃ | H | H |
| 1.16 | H | | O | Cyclopropyl | H | H |
| 1.17 | H | | O | Ph | H | H |
| 1.18 | H | H | H | O | H | H |
| 1.19 | H | H | Cyclopropyl | O | H | H |
| 1.20 | H | H | CH₃ | O | H | H |
| 1.21 | tBuOC(O) | H | —CH₂— | | H | H |
| 1.22 | tBuOC(O) | H | —CH₂—CH₂—CH₂— | | H | H |
| 1.23 | tBuOC(O) | H | —CH=CH—CH₂— | | H | H |
| 1.24 | tBuOC(O) | H | —CH₂—CH=CH— | | H | H |
| 1.25 | tBuOC(O) | H | —CH₂—CH₂—CH₂—CH₂— | | H | H |
| 1.26 | tBuOC(O) | H | —CH=CH—CH₂—CH₂— | | H | H |
| 1.27 | tBuOC(O) | H | —CH₂—CH=CH—CH₂— | | H | H |
| 1.28 | tBuOC(O) | H | —CH₂—CH₂—CH=CH— | | H | H |
| 1.29 | tBuOC(O) | H | H | Ph | H | H |
| 1.30 | tBuOC(O) | H | H | cyclopropyl | H | H |
| 1.31 | tBuOC(O) | H | cyclopropyl | H | H | H |
| 1.32 | tBuOC(O) | H | H | CH₃ | H | H |
| 1.33 | tBuOC(O) | H | CH₃ | H | H | H |
| 1.34 | tBuOC(O) | H | H | H | H | H |
| 1.35 | tBuOC(O) | | O | H | H | H |
| 1.36 | tBuOC(O) | | O | CH₃ | H | H |
| 1.37 | tBuOC(O) | | O | Cyclopropyl | H | H |
| 1.38 | tBuOC(O) | | O | Ph | H | H |
| 1.39 | tBuOC(O) | H | H | O | H | H |
| 1.40 | tBuOC(O) | H | Cyclopropyl | O | H | H |
| 1.41 | tBuOC(O) | H | CH₃ | O | H | H |
| 1.42 | CH₃ | H | —CH₂— | | H | H |
| 1.43 | CH₃ | H | —CH₂—CH₂—CH₂— | | H | H |
| 1.44 | CH₃ | H | —CH=CH—CH₂— | | H | H |
| 1.45 | CH₃ | H | —CH₂—CH=CH— | | H | H |
| 1.46 | CH₃ | H | —CH₂—CH₂—CH₂—CH₂— | | H | H |
| 1.47 | CH₃ | H | —CH=CH—CH₂—CH₂— | | H | H |
| 1.48 | CH₃ | H | —CH₂—CH=CH—CH₂— | | H | H |
| 1.49 | CH₃ | H | —CH₂—CH₂—CH=CH— | | H | H |
| 1.50 | CH₃ | H | H | H | H | H |

TABLE 1-continued

Z = C(R3R5)NR1

(I)

| Compound | R1 | R4 | R2 | R5 | R3 | R7 |
|---|---|---|---|---|---|---|
| 1.51 | CH₃ | H | H | cyclopropyl | H | H |
| 1.52 | CH₃ | H | cyclopropyl | H | H | H |
| 1.53 | CH₃ | H | H | CH₃ | H | H |
| 1.54 | CH₃ | H | CH₃ | H | H | H |
| 1.55 | CH₃ | H | H | H | H | H |
| 1.56 | CH₃ | | O | H | H | H |
| 1.57 | CH₃ | | O | CH₃ | H | H |
| 1.58 | CH₃ | | O | Cyclopropyl | H | H |
| 1.59 | CH₃ | | O | Ph | H | H |
| 1.60 | CH₃ | H | H | O | H | H |
| 1.61 | CH₃ | H | Cyclopropyl | O | H | H |
| 1.62 | CH₃ | H | CH₃ | O | H | H |
| 1.63 | tBuOC(O) | H | —CH₂— | | H | H |
| 1.64 | tBuOC(O) | H | —CH₂—CH₂—CH₂— | | H | H |
| 1.65 | tBuOC(O) | H | —CH=CH—CH₂— | | H | H |
| 1.66 | tBuOC(O) | H | —CH₂—CH=CH— | | H | H |
| 1.67 | tBuOC(O) | H | —CH₂—CH₂—CH₂—CH₂— | | H | H |
| 1.68 | tBuOC(O) | H | —CH=CH—CH₂—CH₂— | | H | H |
| 1.69 | tBuOC(O) | H | —CH₂—CH=CH—CH₂— | | H | H |
| 1.70 | tBuOC(O) | H | —CH₂—CH₂—CH=CH— | | H | H |
| 1.71 | tBuOC(O) | H | H | H | H | H |
| 1.72 | tBuOC(O) | H | H | H | H | H |
| 1.73 | tBuOC(O) | H | cyclopropyl | H | H | H |
| 1.74 | tBuOC(O) | H | H | CH₃ | H | H |
| 1.75 | tBuOC(O) | H | CH₃ | H | H | H |
| 1.76 | tBuOC(O) | H | H | H | H | H |
| 1.77 | tBuOC(O) | | O | H | H | H |
| 1.78 | tBuOC(O) | | O | CH₃ | H | H |
| 1.79 | tBuOC(O) | | O | Cyclopropyl | H | H |
| 1.80 | tBuOC(O) | | O | Ph | H | H |
| 1.81 | tBuOC(O) | H | H | H | H | O |
| 1.82 | tBuOC(O) | H | Cyclopropyl | H | H | O |
| 1.83 | tBuOC(O) | H | CH₃ | H | H | O |
| 1.84 | Ph | H | —CH₂— | | H | H |
| 1.85 | Ph | H | —CH₂—CH₂—CH₂— | | H | H |
| 1.86 | Ph | H | —CH=CH—CH₂— | | H | H |
| 1.87 | Ph | H | —CH₂—CH=CH— | | H | H |
| 1.88 | Ph | H | —CH₂—CH₂—CH₂—CH₂— | | H | H |
| 1.89 | Ph | H | —CH=CH—CH₂—CH₂— | | H | H |
| 1.90 | Ph | H | —CH₂—CH=CH—CH₂— | | H | H |
| 1.91 | Ph | H | —CH₂—CH₂—CH=CH— | | H | H |
| 1.92 | Ph | H | H | H | H | H |
| 1.93 | Ph | H | H | H | H | H |
| 1.94 | Ph | H | cyclopropyl | H | H | H |
| 1.95 | Ph | H | H | H | H | H |
| 1.96 | Ph | H | CH₃ | H | H | H |
| 1.97 | Ph | H | H | H | H | H |
| 1.98 | Ph | | O | H | H | H |
| 1.99 | Ph | | O | CH₃ | H | H |
| 2.00 | Ph | | O | Cyclopropyl | H | H |
| 2.01 | Ph | | O | Ph | H | H |
| 2.03 | Ph | H | H | O | H | H |
| 2.04 | Ph | H | Cyclopropyl | O | H | H |
| 2.05 | Ph | H | CH₃ | O | H | H |
| 2.06 | H | H | —CH₂—CH₂—CH₂— | | H | Me |
| 2.07 | H | H | —CH=CH—CH₂— | | H | Me |
| 2.08 | H | H | —CH₂—CH₂—CH₂— | | H | OMe |
| 2.09 | H | H | —CH=CH—CH₂— | | H | OMe |

TABLE 2

Z = C(R11R12)C(R3R5)NR1

| Compound | R1 | R3 | R5 | R11 | R12 | C(R2R4) |
|---|---|---|---|---|---|---|
| 2.15 | H | H | —CH$_2$— | | H | CH$_2$ |
| 2.16 | H | H | —CH$_2$—CH$_2$—CH$_2$— | | H | CH$_2$ |
| 2.17 | H | H | —CH=CH—CH$_2$— | | H | CH$_2$ |
| 2.18 | H | H | —CH$_2$—CH=CH— | | H | CH$_2$ |
| 2.19 | H | H | —CH$_2$—CH$_2$—CH$_2$—CH$_2$— | | H | CH$_2$ |
| 2.20 | H | H | —CH=CH—CH$_2$—CH$_2$— | | H | CH$_2$ |
| 2.21 | H | H | —CH$_2$—CH=CH—CH$_2$— | | H | CH$_2$ |
| 2.22 | H | H | —CH$_2$—CH$_2$—CH=CH— | | H | CH$_2$ |
| 2.23 | H | H | H | Ph | H | CH$_2$ |
| 2.24 | H | H | Ph | H | H | CH$_2$ |
| 2.25 | H | H | H | cyclopropyl | H | CH$_2$ |
| 2.26 | H | H | cyclopropyl | H | H | CH$_2$ |
| 2.27 | H | H | H | CH$_3$ | H | CH$_2$ |
| 2.28 | H | H | CH$_3$ | H | H | CH$_2$ |
| 2.29 | H | H | H | H | H | CH$_2$ |
| 2.30 | H | | O | H | H | CH$_2$ |
| 2.31 | H | | O | CH$_3$ | H | CH$_2$ |
| 2.32 | H | | O | Cyclopropyl | H | CH$_2$ |
| 2.33 | H | | O | Ph | H | CH$_2$ |
| 2.34 | H | H | H | O | | CH$_2$ |
| 2.35 | H | H | Cyclopropyl | O | | CH$_2$ |
| 2.36 | H | H | Ph | O | | CH$_2$ |
| 2.37 | H | H | CH$_3$ | O | | CH$_2$ |
| 2.38 | H | H | —CH$_2$— | | H | CH(CH$_3$) |
| 2.39 | H | H | —CH$_2$—CH$_2$—CH$_2$— | | H | CH(CH$_3$) |
| 2.40 | H | H | —CH=CH—CH$_2$— | | H | CH(CH$_3$) |
| 2.41 | H | H | —CH$_2$—CH=CH— | | H | CH(CH$_3$) |
| 2.42 | H | H | —CH$_2$—CH$_2$—CH$_2$—CH$_2$— | | H | CH(CH$_3$) |
| 2.43 | H | H | —CH=CH—CH$_2$—CH$_2$— | | H | CH(CH$_3$) |
| 2.44 | H | H | —CH$_2$—CH=CH—CH$_2$— | | H | CH(CH$_3$) |
| 2.45 | H | H | —CH$_2$—CH$_2$—CH=CH— | | H | CH(CH$_3$) |
| 2.46 | H | H | H | Ph | H | CH(CH$_3$) |
| 2.47 | H | H | Ph | H | H | CH(CH$_3$) |
| 2.48 | H | H | H | cyclopropyl | H | CH(CH$_3$) |
| 2.49 | H | H | cyclopropyl | H | H | CH(CH$_3$) |
| 2.50 | H | H | H | CH$_3$ | H | CH(CH$_3$) |
| 2.51 | H | H | CH$_3$ | H | H | CH(CH$_3$) |
| 2.52 | H | H | H | H | H | CH(CH$_3$) |
| 2.53 | H | | O | H | H | CH(CH$_3$) |
| 2.54 | H | | O | CH$_3$ | H | CH(CH$_3$) |
| 2.55 | H | | O | Cyclopropyl | H | CH(CH$_3$) |
| 2.56 | H | | O | Ph | H | CH(CH$_3$) |
| 2.57 | H | H | H | O | | CH(CH$_3$) |
| 2.58 | H | H | Cyclopropyl | O | | CH(CH$_3$) |
| 2.59 | H | H | Ph | O | | CH(CH$_3$) |
| 2.60 | H | H | CH$_3$ | O | | CH(CH$_3$) |
| 2.61 | H | H | H | H | H | C(O) |
| 2.62 | tBuOC(O) | H | —CH$_2$— | | H | CH$_2$ |
| 2.63 | tBuOC(O) | H | —CH$_2$—CH$_2$—CH$_2$— | | H | CH$_2$ |
| 2.64 | tBuOC(O) | H | —CH=CH—CH$_2$— | | H | CH$_2$ |
| 2.65 | tBuOC(O) | H | —CH$_2$—CH=CH— | | H | CH$_2$ |
| 2.66 | tBuOC(O) | H | —CH$_2$—CH$_2$—CH$_2$—CH$_2$— | | H | CH$_2$ |
| 2.67 | tBuOC(O) | H | —CH=CH—CH$_2$—CH$_2$— | | H | CH$_2$ |
| 2.68 | tBuOC(O) | H | —CH$_2$—CH=CH—CH$_2$— | | H | CH$_2$ |
| 2.69 | tBuOC(O) | H | —CH$_2$—CH$_2$—CH=CH— | | H | CH$_2$ |
| 2.70 | tBuOC(O) | H | H | Ph | H | CH$_2$ |
| 2.71 | tBuOC(O) | H | Ph | H | H | CH$_2$ |
| 2.72 | tBuOC(O) | H | H | cyclopropyl | H | CH$_2$ |
| 2.73 | tBuOC(O) | H | cyclopropyl | H | H | CH$_2$ |
| 2.74 | tBuOC(O) | H | H | CH$_3$ | H | CH$_2$ |
| 2.75 | tBuOC(O) | H | CH$_3$ | H | H | CH$_2$ |
| 2.76 | tBuOC(O) | H | H | H | H | CH$_2$ |
| 2.77 | tBuOC(O) | | O | H | H | CH$_2$ |
| 2.78 | tBuOC(O) | | O | CH$_3$ | H | CH$_2$ |
| 2.79 | tBuOC(O) | | O | cyclopropyl | H | CH$_2$ |
| 2.80 | tBuOC(O) | | O | Ph | H | CH$_2$ |
| 2.81 | tBuOC(O) | H | H | O | | CH$_2$ |
| 2.82 | tBuOC(O) | H | Cyclopropyl | O | | CH$_2$ |
| 2.83 | tBuOC(O) | H | Ph | O | | CH$_2$ |
| 2.84 | tBuOC(O) | H | CH$_3$ | O | | CH$_2$ |
| 2.85 | tBuOC(O) | H | —CH$_2$— | | H | CH(CH$_3$) |
| 2.86 | tBuOC(O) | H | —CH$_2$—CH$_2$—CH$_2$— | | H | CH(CH$_3$) |
| 2.87 | tBuOC(O) | H | —CH=CH—CH$_2$— | | H | CH(CH$_3$) |
| 2.88 | tBuOC(O) | H | —CH$_2$—CH=CH— | | H | CH(CH$_3$) |
| 2.89 | tBuOC(O) | H | —CH$_2$—CH$_2$—CH$_2$—CH$_2$— | | H | CH(CH$_3$) |
| 2.90 | tBuOC(O) | H | —CH=CH—CH$_2$—CH$_2$— | | H | CH(CH$_3$) |

TABLE 2-continued

Z = C(R11R12)C(R3R5)NR1

| Compound | R1 | R3 | R5 | R11 | R12 | C(R2R4) |
|---|---|---|---|---|---|---|
| 2.91 | tBuOC(O) | H | —CH$_2$—CH=CH—CH$_2$— | | H | CH(CH$_3$) |
| 2.93 | tBuOC(O) | H | —CH$_2$—CH$_2$—CH=CH— | | H | CH(CH$_3$) |
| 2.94 | tBuOC(O) | H | H | Ph | H | CH(CH$_3$) |
| 2.95 | tBuOC(O) | H | Ph | H | H | CH(CH$_3$) |
| 2.96 | tBuOC(O) | H | H | Cyclopropyl | H | CH(CH$_3$) |
| 2.97 | tBuOC(O) | H | cyclopropyl | H | H | CH(CH$_3$) |
| 2.98 | tBuOC(O) | H | H | CH$_3$ | H | CH(CH$_3$) |
| 2.99 | tBuOC(O) | H | CH$_3$ | H | H | CH(CH$_3$) |
| 3.00 | tBuOC(O) | H | H | H | H | CH(CH$_3$) |
| 3.01 | tBuOC(O) | | O | H | H | CH(CH$_3$) |
| 3.02 | tBuOC(O) | | O | CH$_3$ | H | CH(CH$_3$) |
| 3.03 | tBuOC(O) | | O | cyclopropyl | H | CH(CH$_3$) |
| 3.04 | tBuOC(O) | | O | Ph | H | CH(CH$_3$) |
| 3.05 | tBuOC(O) | H | H | O | | CH(CH$_3$) |
| 3.06 | tBuOC(O) | H | cyclopropyl | O | | CH(CH$_3$) |
| 3.07 | tBuOC(O) | H | Ph | O | | CH(CH$_3$) |
| 3.08 | tBuOC(O) | H | CH$_3$ | O | | CH(CH$_3$) |
| 3.09 | tBuOC(O) | H | H | H | H | C(O) |
| 3.1 | CH$_3$ | H | —CH$_2$— | | H | CH$_2$ |
| 3.11 | CH$_3$ | H | —CH$_2$—CH$_2$—CH$_2$— | | H | CH$_2$ |
| 3.12 | CH$_3$ | H | —CH=CH—CH$_2$— | | H | CH$_2$ |
| 3.13 | CH$_3$ | H | —CH$_2$—CH=CH— | | H | CH$_2$ |
| 3.14 | CH$_3$ | H | —CH$_2$—CH$_2$—CH$_2$—CH$_2$— | | H | CH$_2$ |
| 3.15 | CH$_3$ | H | —CH=CH—CH$_2$—CH$_2$— | | H | CH$_2$ |
| 3.16 | CH$_3$ | H | —CH$_2$—CH=CH—CH$_2$— | | H | CH$_2$ |
| 3.17 | CH$_3$ | H | —CH$_2$—CH$_2$—CH=CH— | | H | CH$_2$ |
| 3.18 | CH$_3$ | H | H | Ph | H | CH$_2$ |
| 3.19 | CH$_3$ | H | Ph | H | H | CH$_2$ |
| 3.2 | CH$_3$ | H | H | cyclopropyl | H | CH$_2$ |
| 3.21 | CH$_3$ | H | cyclopropyl | H | H | CH$_2$ |
| 3.22 | CH$_3$ | H | H | CH$_3$ | H | CH$_2$ |
| 3.23 | CH$_3$ | H | CH$_3$ | H | H | CH$_2$ |
| 3.24 | CH$_3$ | H | H | H | H | CH$_2$ |
| 3.25 | CH$_3$ | | O | H | H | H |
| 3.26 | CH$_3$ | | O | CH$_3$ | H | CH$_2$ |
| 3.27 | CH$_3$ | | O | cyclopropyl | H | CH$_2$ |
| 3.28 | CH$_3$ | | O | Ph | H | CH$_2$ |
| 3.29 | CH$_3$ | H | H | O | | CH$_2$ |
| 3.3 | CH$_3$ | H | cyclopropyl | O | | CH$_2$ |
| 3.31 | CH$_3$ | H | Ph | O | | CH$_2$ |
| 3.32 | CH$_3$ | H | CH$_3$ | O | | CH$_2$ |
| 3.33 | CH$_3$ | H | —CH$_2$— | | H | CH(CH$_3$) |
| 3.34 | CH$_3$ | H | —CH$_2$—CH$_2$—CH$_2$— | | H | CH(CH$_3$) |
| 3.35 | CH$_3$ | H | —CH=CH—CH$_2$— | | H | CH(CH$_3$) |
| 3.36 | CH$_3$ | H | —CH$_2$—CH=CH— | | H | CH(CH$_3$) |
| 3.37 | CH$_3$ | H | —CH$_2$—CH$_2$—CH$_2$—CH$_2$— | | H | CH(CH$_3$) |
| 3.38 | CH$_3$ | H | —CH=CH—CH$_2$—CH$_2$— | | H | CH(CH$_3$) |
| 3.39 | CH$_3$ | H | —CH$_2$—CH=CH—CH$_2$— | | H | CH(CH$_3$) |
| 3.4 | CH$_3$ | H | —CH$_2$—CH$_2$—CH=CH— | | H | CH(CH$_3$) |
| 3.41 | CH$_3$ | H | H | Ph | H | CH(CH$_3$) |
| 3.42 | CH$_3$ | H | Ph | H | H | CH(CH$_3$) |
| 3.43 | CH$_3$ | H | H | cyclopropyl | H | CH(CH$_3$) |
| 3.44 | CH$_3$ | H | cyclopropyl | H | H | CH(CH$_3$) |
| 3.45 | CH$_3$ | H | H | CH$_3$ | H | CH(CH$_3$) |
| 3.46 | CH$_3$ | H | CH$_3$ | H | H | CH(CH$_3$) |
| 3.47 | CH$_3$ | H | H | H | H | CH(CH$_3$) |
| 3.48 | CH$_3$ | | O | H | H | CH(CH$_3$) |
| 3.49 | CH$_3$ | | O | CH$_3$ | H | CH(CH$_3$) |
| 3.5 | CH$_3$ | | O | cyclopropyl | H | CH(CH$_3$) |
| 3.51 | CH$_3$ | | O | Ph | H | CH(CH$_3$) |
| 3.52 | CH$_3$ | H | H | O | | CH(CH$_3$) |
| 3.53 | CH$_3$ | H | cyclopropyl | O | | CH(CH$_3$) |
| 3.54 | CH$_3$ | H | Ph | O | | CH(CH$_3$) |
| 3.55 | CH$_3$ | H | CH$_3$ | O | | CH(CH$_3$) |
| 3.56 | CH$_3$ | H | H | H | H | C(O) |
| 3.57 | Ph | H | —CH$_2$— | | H | CH$_2$ |
| 3.58 | Ph | H | —CH$_2$—CH$_2$—CH$_2$— | | H | CH$_2$ |
| 3.59 | Ph | H | —CH=CH—CH$_2$— | | H | CH$_2$ |
| 3.6 | Ph | H | —CH$_2$—CH=CH— | | H | CH$_2$ |
| 3.61 | Ph | H | —CH$_2$—CH$_2$—CH$_2$—CH$_2$— | | H | CH$_2$ |
| 3.62 | Ph | H | —CH=CH—CH$_2$—CH$_2$— | | H | CH$_2$ |
| 3.63 | Ph | H | —CH$_2$—CH=CH—CH$_2$— | | H | CH$_2$ |
| 3.64 | Ph | H | —CH$_2$—CH$_2$—CH=CH— | | H | CH$_2$ |
| 3.65 | Ph | H | H | H | H | CH$_2$ |
| 3.66 | Ph | H | Ph | H | H | CH$_2$ |
| 3.67 | Ph | H | H | cyclopropyl | H | CH$_2$ |

TABLE 2-continued

Z = C(R11R12)C(R3R5)NR1

| Compound | R1 | R3 | R5 | R11 | R12 | C(R2R4) |
|---|---|---|---|---|---|---|
| 3.68 | Ph | H | cyclopropyl | H | H | CH$_2$ |
| 3.69 | Ph | H | H | CH$_3$ | H | CH$_2$ |
| 3.7 | Ph | H | CH$_3$ | H | H | CH$_2$ |
| 3.71 | Ph | H | H | H | H | CH$_2$ |
| 3.72 | Ph |   | O | H | H | CH$_2$ |
| 3.73 | Ph |   | O | CH$_3$ | H | CH$_2$ |
| 3.74 | Ph |   | O | cyclopropyl | H | CH$_2$ |
| 3.75 | Ph |   | O | Ph | H | CH$_2$ |
| 3.76 | Ph | H | H |   | O | CH$_2$ |
| 3.77 | Ph | H | cyclopropyl |   | O | CH$_2$ |
| 3.78 | Ph | H | Ph |   | O | CH$_2$ |
| 3.79 | Ph | H | CH$_3$ |   | O | CH$_2$ |
| 3.8 | Ph | H | —CH$_2$— |   | H | CH(CH$_3$) |
| 3.81 | Ph | H | —CH$_2$—CH$_2$—CH$_2$— |   | H | CH(CH$_3$) |
| 3.82 | Ph | H | —CH=CH—CH$_2$— |   | H | CH(CH$_3$) |
| 3.83 | Ph | H | —CH$_2$—CH=CH— |   | H | CH(CH$_3$) |
| 3.84 | Ph | H | —CH$_2$—CH$_2$—CH$_2$—CH$_2$— |   | H | CH(CH$_3$) |
| 3.85 | Ph | H | —CH=CH—CH$_2$—CH$_2$— |   | H | CH(CH$_3$) |
| 3.86 | Ph | H | —CH$_2$—CH=CH—CH$_2$— |   | H | CH(CH$_3$) |
| 3.87 | Ph | H | —CH$_2$—CH$_2$—CH=CH— |   | H | CH(CH$_3$) |
| 3.88 | Ph | H | H | Ph | H | CH(CH$_3$) |
| 3.89 | Ph | H | Ph | H | H | CH(CH$_3$) |
| 3.9 | Ph | H | H | cyclopropyl | H | CH(CH$_3$) |
| 3.91 | Ph | H | cyclopropyl | H | H | CH(CH$_3$) |
| 3.92 | Ph | H | H | CH$_3$ | H | CH(CH$_3$) |
| 3.93 | Ph | H | CH$_3$ | H | H | CH(CH$_3$) |
| 3.94 | Ph | H | H | H | H | CH(CH$_3$) |
| 3.95 | Ph |   | O | H | H | CH(CH$_3$) |
| 3.96 | Ph |   | O | CH$_3$ | H | CH(CH$_3$) |
| 3.97 | Ph |   | O | cyclopropyl | H | CH(CH$_3$) |
| 3.98 | Ph |   | O | Ph | H | CH(CH$_3$) |
| 3.99 | Ph | H | H |   | O | CH(CH$_3$) |
| 4.00 | Ph | H | cyclopropyl |   | O | CH(CH$_3$) |
| 4.01 | Ph | H | Ph |   | O | CH(CH$_3$) |
| 4.02 | Ph | H | CH$_3$ |   | O | CH(CH$_3$) |
| 4.03 | Ph | H | H | H | H | C(O) |

TABLE 3

Z = C(R13R14)(R11R12)C(R3R5)NR1

| Compound | R1 | R3 | R5 | C(R11R12) | C(R13R14) | C(R2R4) |
|---|---|---|---|---|---|---|
| 5.00 | H | H | H | CH$_2$ | CH$_2$ | CH$_2$ |
| 5.01 | Me | H | H | CH$_2$ | CH$_2$ | CH$_2$ |
| 5.02 | Ac | H | H | CH$_2$ | CH$_2$ | CH$_2$ |
| 5.03 | Boc | H | H | CH$_2$ | CH$_2$ | CH$_2$ |
| 5.04 | Ph | H | H | CH$_2$ | CH$_2$ | CH$_2$ |
| 5.05 | H | H | Me | CH$_2$ | CH$_2$ | CH$_2$ |
| 5.06 | Me | H | Me | CH$_2$ | CH$_2$ | CH$_2$ |
| 5.07 | Ac | H | Me | CH$_2$ | CH$_2$ | CH$_2$ |
| 5.08 | Boc | H | Me | CH$_2$ | CH$_2$ | CH$_2$ |
| 5.09 | Ph | H | Me | CH$_2$ | CH$_2$ | CH$_2$ |
| 5.10 | H | H | Ph | CH$_2$ | CH$_2$ | CH$_2$ |
| 5.11 | Me | H | Ph | CH$_2$ | CH$_2$ | CH$_2$ |
| 5.12 | Ac | H | Ph | CH$_2$ | CH$_2$ | CH$_2$ |
| 5.13 | Boc | H | Ph | CH$_2$ | CH$_2$ | CH$_2$ |
| 5.14 | Ph | H | Ph | CH$_2$ | CH$_2$ | CH$_2$ |

The compounds of Formula (I) according to the invention can be used as plant growth regulators or seed germination promoters by themselves, but they are generally formulated into plant growth regulation or seed germination promotion compositions using formulation adjuvants, such as carriers, solvents and surface-active agents (SFAs). Thus, the present invention further provides a plant growth regulator composition comprising a plant growth regulation compound of Formula (I) and an agriculturally acceptable formulation adjuvant. The present invention further provides a plant growth regulator composition consisting essentially of a plant growth regulation compound of Formula (I) and an agriculturally acceptable formulation adjuvant. The present invention further provides a plant growth regulator composition consisting of a plant growth regulation compound of Formula (I) and an agriculturally acceptable formulation adjuvant. The present invention further provides a seed germination promoter composition comprising a seed germination promoter compound of Formula (I) and an agriculturally acceptable formulation adjuvant. The present invention further provides a seed germination promoter composition consisting essentially of a seed germination promoter compound of Formula (I) and an agriculturally acceptable formulation adjuvant. The present invention further provides a seed germination promoter composition consisting of a seed germination promoter compound of Formula (I) and an agriculturally acceptable formulation adjuvant. The composition can be in the form of concentrates which are diluted prior to use, although ready-to-use compositions can also be made. The final dilution is usually made with water, but can be made instead of, or in addition to, water, with, for example, liquid fertilisers, micronutrients, biological organisms, oil or solvents.

The compositions generally comprise from 0.1 to 99% by weight, especially from 0.1 to 95% by weight, compounds of Formula (I) and from 1 to 99.9% by weight of a formulation adjuvant which preferably includes from 0 to 25% by weight of a surface-active sub stance.

The compositions can be chosen from a number of formulation types, many of which are known from the Manual on Development and Use of FAO Specifications for Plant Protection Products, 5th Edition, 1999. These include dustable powders (DP), soluble powders (SP), water soluble granules (SG), water dispersible granules (WG), wettable powders (WP), granules (GR) (slow or fast release), soluble concentrates (SL), oil miscible liquids (OL), ultra low volume liquids (UL), emulsifiable concentrates (EC), dispersible concentrates (DC), emulsions (both oil in water (EW) and water in oil (EO)), microemulsions (ME), suspension concentrates (SC), aerosols, capsule suspensions (CS) and seed treatment formulations. The formulation type chosen in any instance will depend upon the particular purpose envisaged and the physical, chemical and biological properties of the compound of Formula (I).

Dustable powders (DP) may be prepared by mixing a compound of Formula (I) with one or more solid diluents (for example natural clays, kaolin, pyrophyllite, bentonite, alumina, montmorillonite, kieselguhr, chalk, diatomaceous earths, calcium phosphates, calcium and magnesium carbonates, sulphur, lime, flours, talc and other organic and inorganic solid carriers) and mechanically grinding the mixture to a fine powder.

Soluble powders (SP) may be prepared by mixing a compound of Formula (I) with one or more water-soluble inorganic salts (such as sodium bicarbonate, sodium carbonate or magnesium sulphate) or one or more water-soluble organic solids (such as a polysaccharide) and, optionally, one or more wetting agents, one or more dispersing agents or a mixture of said agents to improve water dispersibility/solubility. The mixture is then ground to a fine powder. Similar compositions may also be granulated to form water soluble granules (SG).

Wettable powders (WP) may be prepared by mixing a compound of Formula (I) with one or more solid diluents or carriers, one or more wetting agents and, preferably, one or more dispersing agents and, optionally, one or more suspending agents to facilitate the dispersion in liquids. The mixture is then ground to a fine powder. Similar compositions may also be granulated to form water dispersible granules (WG).

Granules (GR) may be formed either by granulating a mixture of a compound of Formula (I) and one or more powdered solid diluents or carriers, or from pre-formed blank granules by absorbing a compound of Formula (I) (or a solution thereof, in a suitable agent) in a porous granular material (such as pumice, attapulgite clays, fuller's earth, kieselguhr, diatomaceous earths or ground corn cobs) or by adsorbing a compound of Formula (I) (or a solution thereof, in a suitable agent) on to a hard core material (such as sands, silicates, mineral carbonates, sulphates or phosphates) and drying if necessary. Agents which are commonly used to aid absorption or adsorption include solvents (such as aliphatic and aromatic petroleum solvents, alcohols, ethers, ketones and esters) and sticking agents (such as polyvinyl acetates, polyvinyl alcohols, dextrins, sugars and vegetable oils). One or more other additives may also be included in granules (for example an emulsifying agent, wetting agent or dispersing agent).

Dispersible Concentrates (DC) may be prepared by dissolving a compound of Formula (I) in water or an organic solvent, such as a ketone, alcohol or glycol ether. These solutions may contain a surface active agent (for example to improve water dilution or prevent crystallisation in a spray tank).

Emulsifiable concentrates (EC) or oil-in-water emulsions (EW) may be prepared by dissolving a compound of Formula (I) in an organic solvent (optionally containing one or more wetting agents, one or more emulsifying agents or a mixture of said agents). Suitable organic solvents for use in ECs include aromatic hydrocarbons (such as alkylbenzenes or alkylnaphthalenes, exemplified by SOLVESSO 100, SOLVESSO 150 and SOLVESSO 200; SOLVESSO is a Registered Trade Mark), ketones (such as cyclohexanone or methylcyclohexanone) and alcohols (such as benzyl alcohol, furfuryl alcohol or butanol), N-alkylpyrrolidones (such as N-methylpyrrolidone or N-octylpyrrolidone), dimethyl amides of fatty acids (such as $C_8$-$C_{10}$ fatty acid dimethylamide) and chlorinated hydrocarbons. An EC product may spontaneously emulsify on addition to water, to produce an emulsion with sufficient stability to allow spray application through appropriate equipment.

Preparation of an EW involves obtaining a compound of Formula (I) either as a liquid (if it is not a liquid at room temperature, it may be melted at a reasonable temperature, typically below 70° C.) or in solution (by dissolving it in an appropriate solvent) and then emulsifying the resultant liquid or solution into water containing one or more SFAs, under high shear, to produce an emulsion. Suitable solvents for use in EWs include vegetable oils, chlorinated hydrocarbons (such as chlorobenzenes), aromatic solvents (such as alkylbenzenes or alkylnaphthalenes) and other appropriate organic solvents which have a low solubility in water.

Microemulsions (ME) may be prepared by mixing water with a blend of one or more solvents with one or more SFAs, to produce spontaneously a thermodynamically stable isotropic liquid formulation. A compound of Formula (I) is present initially in either the water or the solvent/SFA blend. Suitable solvents for use in MEs include those hereinbefore described for use in ECs or in EWs. An ME may be either an oil-in-water or a water-in-oil system (which system is present may be determined by conductivity measurements) and may be suitable for mixing water-soluble and oil-soluble pesticides in the same formulation. An ME is suitable for dilution into water, either remaining as a microemulsion or forming a conventional oil-in-water emulsion.

Suspension concentrates (SC) may comprise aqueous or non-aqueous suspensions of finely divided insoluble solid particles of a compound of Formula (I). SCs may be prepared by ball or bead milling the solid compound of Formula (I) in a suitable medium, optionally with one or more dispersing agents, to produce a fine particle suspension of the compound. One or more wetting agents may be included in the composition and a suspending agent may be included to reduce the rate at which the particles settle. Alternatively, a compound of Formula (I) may be dry milled and added to water, containing agents hereinbefore described, to produce the desired end product.

Aerosol formulations comprise a compound of Formula (I) and a suitable propellant (for example n-butane). A compound of Formula (I) may also be dissolved or dispersed in a suitable medium (for example water or a water miscible liquid, such as n-propanol) to provide compositions for use in non-pressurised, hand-actuated spray pumps.

Capsule suspensions (CS) may be prepared in a manner similar to the preparation of EW formulations but with an additional polymerisation stage such that an aqueous dispersion of oil droplets is obtained, in which each oil droplet is encapsulated by a polymeric shell and contains a compound of Formula (I) and, optionally, a carrier or diluent therefor. The polymeric shell may be produced by either an interfacial polycondensation reaction or by a coacervation procedure. The compositions may provide for controlled release of the compound of Formula (I) and they may be used for seed treatment. A compound of Formula (I) may also be formulated in a biodegradable polymeric matrix to provide a slow, controlled release of the compound.

The composition may include one or more additives to improve the biological performance of the composition, for example by improving wetting, retention or distribution on surfaces; resistance to rain on treated surfaces; or uptake or mobility of a compound of Formula (I). Such additives include surface active agents (SFAs), spray additives based on oils, for example certain mineral oils or natural plant oils (such as soy bean and rape seed oil), and blends of these with other bio-enhancing adjuvants (ingredients which may aid or modify the action of a compound of Formula (I)).

Wetting agents, dispersing agents and emulsifying agents may be SFAs of the cationic, anionic, amphoteric or non-ionic type.

Suitable SFAs of the cationic type include quaternary ammonium compounds (for example cetyltrimethyl ammonium bromide), imidazolines and amine salts.

Suitable anionic SFAs include alkali metals salts of fatty acids, salts of aliphatic monoesters of sulphuric acid (for example sodium lauryl sulphate), salts of sulphonated aromatic compounds (for example sodium dodecylbenzenesulphonate, calcium dodecylbenzenesulphonate, butylnaphthalene sulphonate and mixtures of sodium di-isopropyl- and tri-isopropyl-naphthalene sulphonates), ether sulphates, alcohol ether sulphates (for example sodium laureth-3-sulphate), ether carboxylates (for example sodium laureth-3-carboxylate), phosphate esters (products from the reaction between one or more fatty alcohols and phosphoric acid (predominately mono-esters) or phosphorus pentoxide (predominately di-esters), for example the reaction between lauryl alcohol and tetraphosphoric acid; additionally these products may be ethoxylated), sulphosuccinamates, paraffin or olefine sulphonates, taurates and lignosulphonates.

Suitable SFAs of the amphoteric type include betaines, propionates and glycinates.

Suitable SFAs of the non-ionic type include condensation products of alkylene oxides, such as ethylene oxide, propylene oxide, butylene oxide or mixtures thereof, with fatty alcohols (such as oleyl alcohol or cetyl alcohol) or with alkylphenols (such as octylphenol, nonylphenol or octylcresol); partial esters derived from long chain fatty acids or hexitol anhydrides; condensation products of said partial esters with ethylene oxide; block polymers (comprising ethylene oxide and propylene oxide); alkanolamides; simple esters (for example fatty acid polyethylene glycol esters); amine oxides (for example lauryl dimethyl amine oxide); and lecithins.

Suitable suspending agents include hydrophilic colloids (such as polysaccharides, polyvinylpyrrolidone or sodium carboxymethylcellulose) and swelling clays (such as bentonite or attapulgite).

The present invention still further provides a method for regulating the growth of plants in a locus, wherein the method comprises application to the locus of a plant growth regulating amount of a composition according to the present invention.

The present invention also provides a method for promoting the germination of seeds, comprising applying to the seeds, or to a locus containing seeds, a seed germination promoting amount of a composition according to the present invention.

The application is generally made by spraying the composition, typically by tractor mounted sprayer for large areas, but other methods such as dusting (for powders), drip or drench can also be used. Alternatively the composition may be applied in furrow or directly to a seed before or at the time of planting.

The compound of Formula (I) or composition of the present invention may be applied to a plant, part of the plant, plant organ, plant propagation material or a surrounding area thereof.

In one embodiment, the invention relates to a method of treating a plant propagation material comprising applying to the plant propagation material a composition of the present invention in an amount effective to promote germination and/or regulate plant growth. The invention also relates to a plant propagation material treated with a compound of Formula (I) or a composition of the present invention. Preferably, the plant propagation material is a seed.

The term "plant propagation material" denotes all the generative parts of the plant, such as seeds, which can be used for the multiplication of the latter and vegetative plant materials such as cuttings and tubers. In particular, there may be mentioned the seeds, roots, fruits, tubers, bulbs, and rhizomes.

Methods for applying active ingredients to plant propagation material, especially seeds, are known in the art, and include dressing, coating, pelleting and soaking application methods of the propagation material. The treatment can be applied to the seed at any time between harvest of the seed and sowing of the seed or during the sowing process. The seed may also be primed either before or after the treatment. The compound of formula (I) may optionally be applied in combination with a controlled release coating or technology so that the compound is released over time.

The composition of the present invention may be applied pre-emergence or post-emergence. Suitably, where the composition is being used to regulate the growth of crop plants, it may be applied pre or post-emergence, but preferably post-emergence of the crop. Where the composition is used to promote the germination of seeds, it may be applied pre-emergence.

The rates of application of compounds of Formula (I) may vary within wide limits and depend on the nature of the soil, the method of application (pre- or post-emergence; seed dressing; application to the seed furrow; no tillage application etc.), the crop plant, the prevailing climatic conditions, and other factors governed by the method of application, the time of application and the target crop. For foliar or drench application, the compounds of Formula (I) according to the invention are generally applied at a rate of from 1 to 2000 g/ha, especially from 5 to 1000 g/ha. For seed treatment the rate of application is generally between 0.0005 and 150 g per 100 kg of seed.

Plants in which the composition according to the invention can be used include crops such as cereals (for example wheat, barley, rye, oats); beet (for example sugar beet or fodder beet); fruits (for example pomes, stone fruits or soft fruits, such as apples, pears, plums, peaches, almonds, cherries, strawberries, raspberries or blackberries); leguminous plants (for example beans, lentils, peas or soybeans); oil plants (for example rape, mustard, poppy, olives, sunflowers, coconut, castor oil plants, cocoa beans or groundnuts); cucumber plants (for example marrows, cucumbers or melons); fibre plants (for example cotton, flax, hemp or jute); citrus fruit (for example oranges, lemons, grapefruit or mandarins); vegetables (for example spinach, lettuce, asparagus, cabbages, carrots, onions, tomatoes, potatoes, cucurbits or paprika); lauraceae (for example avocados, cinnamon or camphor); maize; rice; tobacco; nuts; coffee; sugar cane; tea; vines; hops; durian; bananas; natural rubber plants; turf or ornamentals (for example flowers, shrubs, broad-leaved trees or evergreens such as conifers). This list does not represent any limitation.

The invention may also be used to regulate the growth, or promote the germination of seeds of non-crop plants, for example to facilitate weed control by synchronizing germination.

Crops are to be understood as also including those crops which have been modified by conventional methods of breeding or by genetic engineering. For example, the invention may be used in conjunction with crops that have been rendered tolerant to herbicides or classes of herbicides (e.g. ALS-, GS-, EPSPS-, PPO-, ACCase- and HPPD-inhibitors). An example of a crop that has been rendered tolerant to imidazolinones, e.g. imazamox, by conventional methods of breeding is Clearfield® summer rape (canola). Examples of crops that have been rendered tolerant to herbicides by genetic engineering methods include e.g. glyphosate- and glufosinate-resistant maize varieties commercially available under the trade names RoundupReady® and LibertyLink®. Methods of rending crop plants tolerant to HPPD-inhibitors are known, for example from WO0246387; for example the crop plant is transgenic in respect of a polynucleotide comprising a DNA sequence which encodes an HPPD-inhibitor resistant HPPD enzyme derived from a bacterium, more particularly from *Pseudomonas fluorescens* or *Shewanella colwelliana*, or from a plant, more particularly, derived from a monocot plant or, yet more particularly, from a barley, maize, wheat, rice, *Brachiaria, Chenchrus, Lolium, Festuca, Setaria, Eleusine, Sorghum* or *Avena* species.

Crops are also to be understood as being those which have been rendered resistant to harmful insects by genetic engineering methods, for example Bt maize (resistant to European corn borer), Bt cotton (resistant to cotton boll weevil) and also Bt potatoes (resistant to Colorado beetle). Examples of Bt maize are the Bt 176 maize hybrids of NK® (Syngenta Seeds). The Bt toxin is a protein that is formed naturally by *Bacillus thuringiensis* soil bacteria. Examples of toxins, or transgenic plants able to synthesise such toxins, are described in EP-A-451 878, EP-A-374 753, WO 93/07278, WO 95/34656, WO 03/052073 and EP-A-427 529. Examples of transgenic plants comprising one or more genes that code for an insecticidal resistance and express one or more toxins are KnockOut® (maize), Yield Gard® (maize), NuCOTIN33B® (cotton), Bollgard® (cotton), NewLeaf® (potatoes), Nature-Gard® and Protexcta®. Plant crops or seed material thereof can be both resistant to herbicides and, at the same time, resistant to insect feeding ("stacked" transgenic events). For example, seed can have the ability to express an insecticidal Cry3 protein while at the same time being tolerant to glyphosate.

Crops are also to be understood to include those which are obtained by conventional methods of breeding or genetic engineering and contain so-called output traits (e.g. improved storage stability, higher nutritional value and improved flavour).

Compounds and compositions of the present invention may be applied in combination with other active ingredients or products for use in agriculture, including insecticides, fungicides, herbicides, plant growth regulators, crop enhancing compounds, nutrients and biologicals. Examples of suitable mixing partners may be found in the Pesticide Manual, 15th edition (published by the British Crop Protection Council). Such mixtures may be applied to a plant, plant propagation material or plant growing locus either simultaneously (for example as a pre-formulated mixture or a tank mix), or sequentially in a suitable timescale. Co-application of pesticides with the present invention has the added benefit of minimising farmer time spent applying products to crops.

The compounds of the invention may be made by the following methods.

SCHEME 1

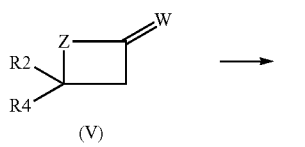

(V)

Z = NH, C(R3R5)NH, C(R11R12) C(R3R5)NH, C(R13R14)C(R11R12)C(R3R5)NH

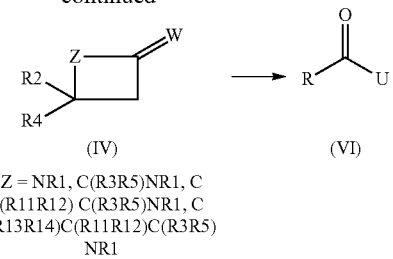

Z = NR1, C(R3R5)NR1, C(R11R12) C(R3R5)NR1, C(R13R14)C(R11R12)C(R3R5)NR1

Compounds of Formula (IV), wherein R1 is alkyl derivatives, may be prepared from a compound of Formula (V) via alkylation by reaction of the amine with an alkylating agent such as an alkyl halide, benzyl halide optionally in the presence of a base such as sodium hydride.

Compounds of formula (IV), wherein R1 is an aromatic or heteroaromatic group, may be prepared from a compound of formula (V) by reaction of the amide with an aromatic or heteroaromatic compound of formula ArX, X being an halogen, in the presence of a base such as potassium phosphate and a suitable catalyst, often a copper (I) salt and a ligand such as dimethylethane-1,2-diamine.

Compounds of Formula (IV), wherein R1 is a carbonyl derivative, may be prepared from a compound of Formula (V) via acylation with a compound of Formula (VI), wherein U is OH, in the presence of a coupling reagent, such as DCC (N,N'-dicyclohexylcarbodiimide), EDC (1-ethyl-3-[3-dimethylamino-propyl]carbodiimide hydrochloride) or BOP-Cl (bis(2-oxo-3-oxazolidinyl)phosphonic chloride), in the presence of a base, such as pyridine, triethylamine, 4-(dimethylamino)pyridine or diisopropylethylamine, and optionally in the presence of a nucleophilic catalyst, such as hydroxybenzotriazole. Optionally, when U is Cl or OC(O)$C_1$-$C_6$ alkoxy, the acylation reaction may be carried out under basic conditions (for example in the presence of pyridine, triethylamine, 4-(dimethylamino)pyridine or diisopropylethylamine), optionally in the presence of a nucleophilic catalyst. Alternatively, the reaction may be conducted in a biphasic system comprising an organic solvent, preferably ethyl acetate, and an aqueous solvent, preferably a solution of sodium bicarbonate. Optionally, when U is $C_1$-$C_6$alkoxy, the amide may be prepared by heating the ester analogue of compound Formula (VI) and amide (V) together. R may be alkyl or alkoxy group.

SCHEME 2

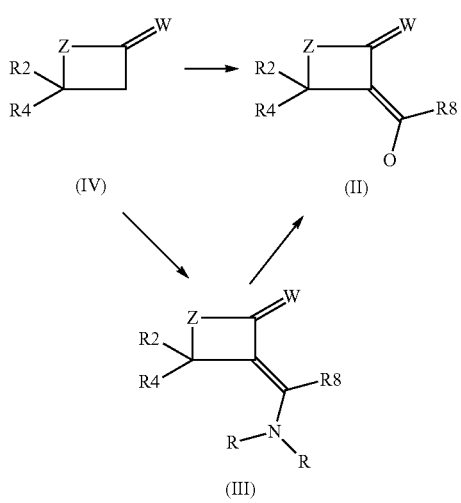

Compounds of Formula (II) may be prepared from a compound of Formula (IV) via reaction with a formic ester derivative such as ethyl formate when R8 is hydrogen in presence of a base such as lithium diisopropylamide or lithium bis(trimethylsilyl)amide. Alternatively, compounds of Formula (II) may be prepared from a compound of Formula (III) via hydrolysis with an acid such as hydrogen chloride. Compounds of Formula (III) wherein R8 is hydrogen may be prepared from compounds of Formula (IV) via reaction with a Bredereck's reagent (t-butoxybis-(dimethylamino) methane) wherein R is methyl or analogue.

Alternatively, Compounds of Formula (II) may be prepared from a compound of Formula (IV) via reaction with an activated acid derivative like an ester or an acid halide such as benzoic acid chloride or methyl acetate in presence of a base such as lithium diisopropylamide or lithium bis(trimethylsilyl)amide.

Alternatively, Compounds of Formula (II) may be prepared from a compound of Formula (IV) via reaction with a aldehyde derivative such as formaldehyde in presence of a base such as lithium diisopropylamide or lithium bis(trimethylsilyl)amide followed by oxidation of the obtained alcohol by methods known to a person skilled in the art.

SCHEME 3

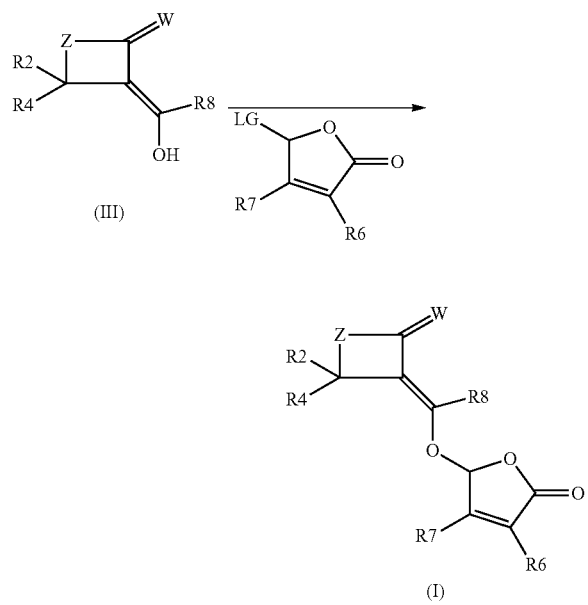

Compounds of Formula (I) may be prepared from a compounds of Formula (II) via nucleophilic substitution of a 5H-furanone derivative having a leaving group (LG) and LG is a leaving group, such as bromine or a chlorine in presence of a base such as for example potassium tert-butylate or triethylamine, with or without a crown ether such as 18-crown-6.

SCHEME 4

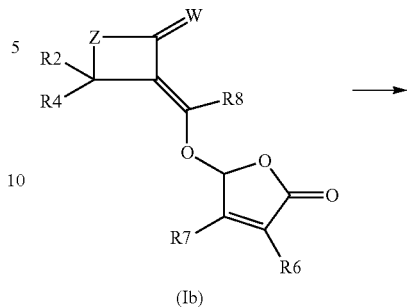

(Ib)

Z = NR1, C(R3R5)NR1, C(R11R12) C(R3R5)NR1, C(R13R14)C(R11R12)C(R3R5)NR1

(Ia)

Z = NH, C(R3R5)NH, C(R11R12) C(R3R5)NH, C(R13R14)C(R11R12)C(R3R5)NH

Alternatively, compounds of Formula (Ia), may be prepared from Formula (Ib) wherein R1 is a protecting group such as tertbutoxycarbonyl by deprotection using an acid such as trifluoroacetic acid or hydrogen chloride or a Lewis acid such as magnesium chloride.

Scheme 5:

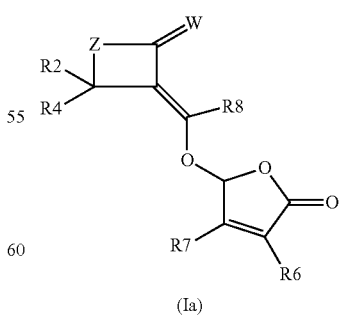

(Ia)

Z = NH, C(R3R5)NH, C(R11R12) C(R3R5)NH, C(R13R14)C(R11R12)C(R3R5)NH

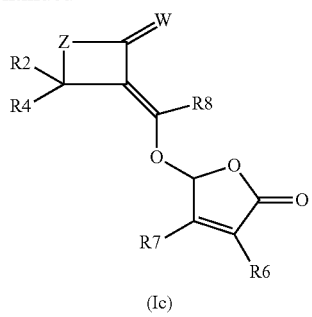

(Ic)

Z = NR1, C(R3R5)NR1, C(R11R12) C(R3R5)NR1, C(R13R14)C(R11R12)C(R3R5)NR1

Compounds of Formula (Ic) wherein R1 is alkyl group, may be prepared from Formula (Ia) by reaction with an alkylating agent of formula R1X, wherein X is a leaving group such as halogen, tosyl or mesyl, in the presence of a base such as sodium hydride or silver oxide.

Compounds of Formula (Ic) wherein R1 is an alkyl carbonyl or alkoxy carbonyl group can be prepared from compounds of Formula (Ia) by reaction with the corresponding acid chloride of formula R1Cl or the corresponding anhydride of formula $R1_2O$, in the presence of a base such as Hunig's base, triethyl amine or sodium carbonate, optionally in the presence of a nucleophile catalyst such as dimethylaminopyridine.

Scheme 6:

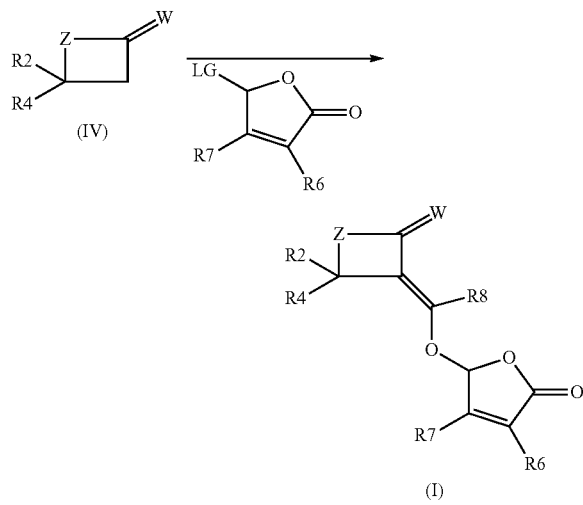

Compounds of Formula (I) may be prepared from a compounds of Formula (IV), via reaction with a formic ester derivative such as ethyl formate when R8 is hydrogen in presence of a base such as lithium diisopropylamide or lithium bis(trimethylsilyl)amide followed by in situ nucleophilic substitution of a 5H-furanone derivative having a leaving group (LG) and LG is a leaving group, such as bromine or a chloride. This reaction is usually carried out at a temperature comprised between −78° C. and 0° C.

Scheme 7:

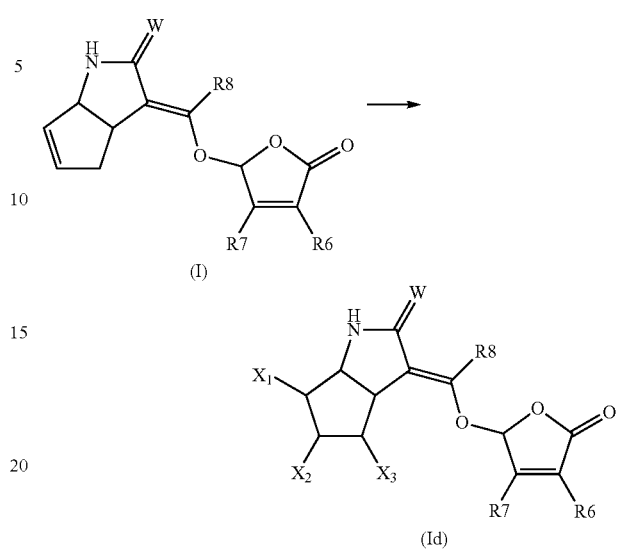

Compounds of formula (Id), wherein X1, X2 and X3 are each independently OH, OAc or form a double bond can be prepared from compounds of formula (I) by reaction with an oxidant such as selenium dioxide or osmium tetroxide, in the presence or not of a co-oxidant such as N-methyl morpholine-N-oxide. Compounds of formula (Id) wherein X1, X2 and X3 are each independently OAc can be prepared from compounds of formula (Id) wherein X1, X2 and X3 are each independently OH by acylation with acetyl chloride or acetic anhydride, in the presence of an organic base such as pyridine or triethylamine and in the presence or not of a nucleophilic catalyst such as dimethylaminopyridine.

EXAMPLES

The following HPLC-MS methods were used for the analysis of the compounds:

Method A: Spectra were recorded on a SQD Mass Spectrometer from Waters (Single quadrupole mass spectrometer) mass spectrometer equipped with an electrospray source (Polarity: positive and negative ions, Capillary: 3.00 kV, Cone: 30.00 V, Extractor: 2.00 V, Source Temperature: 150° C., Desolvation Temperature: 250° C., Cone Gas Flow: 0 L/Hr, Desolvation Gas Flow: 650 L/Hr, Mass range: 100 to 900 Da) and an Acquity UPLC from Waters (Binary pump, heated column compartment and diode-array detector, Solvent degasser, binary pump, heated column compartment and diode-array detector, Column: Phenomenex Gemini C18, 3 µm, 30×2 mm, Temp: 60° C., flow rate 0.85 mL/min; DAD Wavelength range (nm): 210 to 500); Solvent Gradient: A=$H_2O$+5% MeOH+0.05% HCOOH, B=Acetonitrile+ 0.05% HCOOH; gradient: 0 min 0% B; 0-1.2 min 100% B; 1.2-1.50 min 100% B.

Method B: Spectra were recorded on a SQD Mass Spectrometer from Waters (Single quadrupole mass spectrometer) mass spectrometer equipped with an electrospray source (Polarity: positive and negative ions, Capillary: 3.00 kV, Cone: 45.00 V, Extractor: 2.00 V, Source Temperature: 150° C., Desolvation Temperature: 250° C., Cone Gas Flow: 0 L/Hr, Desolvation Gas Flow: 650 L/Hr, Mass range: 100 to 900 Da) and an Acquity UPLC from Waters (Binary pump, heated column compartment and diode-array detector, Solvent degasser, binary pump, heated column compartment and diode-array detector, Column: Waters UPLC HSS T3, 1.8 µm, 30×2.1 mm, Temp: 60° C., flow rate 0.85 mL/min; DAD Wavelength range (nm): 210 to 500); Solvent Gradient: A=H$_2$O+5% MeOH+0.05% HCOOH, B=Acetonitrile+ 0.05% HCOOH; gradient: 0 min 10% B; 0-1.2 min 100% B; 1.2-1.50 min 100% B Method C: Spectra were recorded on a SQD Mass Spectrometer from Waters (Single quadrupole mass spectrometer) mass spectrometer equipped with an electrospray source (Polarity: positive and negative ions, Capillary: 3.00 kV, Cone: 30.00 V, Extractor: 2.00 V, Source Temperature: 150° C., Desolvation Temperature: 250° C., Cone Gas Flow: 0 L/Hr, Desolvation Gas Flow: 650 L/Hr, Mass range: 100 to 900 Da) and an Acquity UPLC from Waters (Binary pump, heated column compartment and diode-array detector, Solvent degasser, binary pump, heated column compartment and diode-array detector, Column: Waters UPLC HSS T3, 1.8 µm, 30×2.1 mm, Temp: 60° C., flow rate 0.85 mL/min; DAD Wavelength range (nm): 210 to 500); Solvent Gradient: A=H$_2$O+5% MeOH+0.05% HCOOH, B=Acetonitrile+ 0.05% HCOOH; gradient: 0 min 10% B; 0-1.2 min 100% B; 1.2-1.50 min 100% B Method D: Spectra were recorded on a ZQ Mass Spectrometer from Waters (Single quadrupole mass spectrometer) equipped with an electrospray source (Polarity: positive or negative ions, Capillary: 3.00 kV, Cone: 30.00 V, Extractor: 2.00 V, Source Temperature: 100° C., Desolvation Temperature: 250° C., Cone Gas Flow: 50 L/Hr, Desolvation Gas Flow: 400 L/Hr, Mass range: 100 to 900 Da) and an Acquity UPLC from Waters (Solvent degasser, binary pump, heated column compartment and diode-array detector. Column: Waters UPLC HSS T3, 1.8 µm, 30×2.1 mm, Temp: 60° C., flow rate 0.85 mL/min; DAD Wavelength range (nm): 210 to 500) Solvent Gradient: A=H$_2$O+5% MeOH+0.05% HCOOH, B=Acetonitrile+0.05% HCOOH) gradient: 0 min 10% B; 0-1.2 min 100% B; 1.2-1.50 min 100% B The following abbreviations are used throughout this section: s=singlet; bs=broad singlet; d=doublet; dd=double doublet; dt=double triplet; t=triplet; tt=triple triplet, q=quartet, m=multiplet; Me=methyl; Et=ethyl; Pr=propyl; Bu=butyl; M.p.=melting point; RT=retention time, M+H$^+$=molecular cation (i.e. measured molecular weight).

Example 1

Tert-butyl 2-oxo-3,3a,4,6a-tetrahydrocyclopenta[b]pyrrole-1-carboxylate IV-1

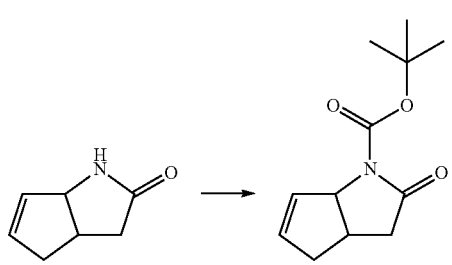 [SMILES: O=C1CC2CC=CC2N1 ; CC(C)(C)OC(=O)N1C(=O)CC2CC=CC21]

To a solution of 3,3a,4,6a-tetrahydro-1H-cyclopenta[b]pyrrol-2-one (340 mg, 2.76 mmol, as prepared in *J. Org. Chem.* 1988, 53, 4006-4014) in CH$_2$Cl$_2$ (27 mL) was added di-tert-butyl dicarbonate (1.9 mL, 8.28 mmol), Et$_3$N (1.16 mL, 8.28 mmol) and N,N-dimethylaminopyridine (34 mg, 0.27 mmol) The solution was stirred for 5 h. It was then poured into water and extracted with CH$_2$Cl$_2$. The combined organic layers were washed with brine, dried, concentrated and crude residue was purified by flash chromatography (2% MeOH in CH$_2$Cl$_2$) giving the desired compound as a yellow oil (502 mg, 89%); $^1$H NMR (400 MHz, CDCl$_3$) 5.51 (2H, m), 5.00 (1H, d), 3.89 (1H, m), 3.78 (1H, dd), 3.70 (1H, m), 2.29 (1H, dd), 2.22 (1H, m), 1.51 (9H, s).

A similar procedure was used to prepare following compounds:
  tert-butyl 2-oxo-5-phenyl-pyrrolidine-1-carboxylate IV-2 was prepared from 5-phenyl-pyrrolidin-2-one; LCMS (Method D): 0.94 min; ES+325 (M+MeCN+Na$^+$).
  tert-butyl 2-oxo-6-phenyl-piperidine-1-carboxylate IV-3 was prepared from 6-phenylpiperidin-2-one; LCMS (Method D): 0.98 min; ES+339 (M+MeCN+Na$^+$).
  tert-butyl 2-oxo-6-methyl-piperidine-1-carboxylate IV-4 was prepared from 6-methylpiperidin-2-one; LCMS (Method D): 0.86 min; ES+236 (M+Na$^+$).

tert-butyl-3-(dimethylaminomethylene)-2-oxo-4,6a-dihydro-3aH-cyclopenta[b]pyrrole-1-carboxylate III-1

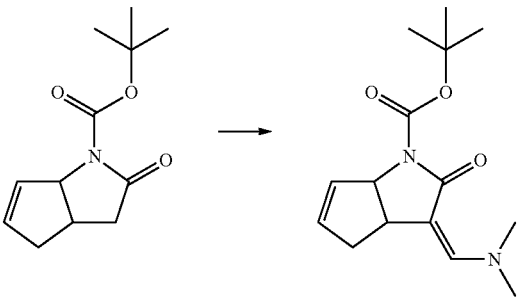 [SMILES: CC(C)(C)OC(=O)N1C(=O)CC2CC=CC21 ; CN(C)/C=C1\C(=O)N(C(=O)OC(C)(C)C)C2C=CCC12]

To a solution of tert-butyl 2-oxo-3,3a,4,6a-tetrahydrocyclopenta[b]pyrrole-1-carboxylate IV-1 (500 mg, 2.23 mmol) in toluene (11 mL) was added tert-butoxybis(dimethylamino)methane (1.39 mL, 6.71 mmol) The solution was heated for 2 h at 110° C. It was then cooled to room temperature, poured into water (20 mL), diluted with ethyl acetate (20 mL), and extracted 3 times. The combined organic layers were washed with brine, dried, concentrated and purified by flash chromatography (5% MeOH in CH$_2$Cl$_2$) giving the desired compound as a brown solid (367 mg, 58%); $^1$H NMR (400 MHz, CDCl$_3$) 7.12 (1H, s), 5.99 (1H, m), 5.85 (1H, m), 4.91 (1H, d), 3.70 (1H, m), 3.03 (6H, s), 2.79 (1H, m), 2.40 (1H, dd), 1.54 (9H, s); LCMS (Method A): 0.83 min; ES+279 (M+H$^+$).

A similar procedure was used to prepare following compounds:
  tert-butyl (3Z)-3-(dimethylaminomethylene)-2-oxo-4,5,6,6a-tetrahydro-3aH-cyclopenta[b]pyrrole-1-carboxylate III-2 was prepared from tert-butyl 2-oxo-3,3a,4,5,6,6a-hexahydrocyclopenta[b]pyrrole-1-carboxylate (Ref Journal of the Chemical Society, Perkin Transactions 1, (7), 706-710; 2001); $^1$H NMR (400 MHz, CDCl$_3$) 7.10 (1H, s), 4.31 (1H, m), 3.42 (1H, m), 3.04 (6H, s), 1.89 (3H, m), 1.58 (3H, m), 1.53 (9H, s). LCMS (Method A): 0.86 min; ES+583 (2M+Na$^+$).
  3-(dimethylaminomethylene)-1-phenyl-pyrrolidin-2-one III-3 from 1-phenyl-pyrrolidin-2-one (commercially available); $^1$H NMR (400 MHz, CDCl$_3$) 7.69 (2H, d), 7.33 (2H, t), 7.08 (2H, m), 3.75 (2H, dd), 3.05 (2H, m), 3.01 (6H, s); LCMS (Method C): 0.67 min, ES+465 (2M+Na⁺).

3-(dimethylaminomethylene)-5-methyl-1-phenyl-pyrrolidin-2-one III-4 from 5-methyl-1-phenyl-pyrrolidin-2-one (as described in *Org. Lett.* 2007, 9, 5477-5480; ¹H NMR (400 MHz, CDCl₃) 7.52 (2H, m), 7.40 (2H, m), 7.10 (1H, s), 7.05 (1H, m), 4.31 (1H, m), 3.01 (6H, s), 2.65 (1H, m), 1.24 (3H, d); LCMS (Method C): 0.70 min, ES+493 (2M+Na⁺).

3-(dimethylaminomethylene)-1-phenyl-piperidin-2-one III-5 from 1-phenyl-piperidin-2-one (prepared as in *Tetrahedron Lett.* 2011, 52, 1169-1172); ¹H NMR (400 MHz, CDCl₃) 7.49 (1H, s), 7.38-7.25 (4H, m), 7.17 (1H, t), 3.64 (2H, m), 3.01 (6H, s), 2.79 (2H, m), 1.95 (2H, m). LCMS (Method B): 0.70 min; ES+204 (M-NMe₂+OH+H⁺).

tert-butyl (3E)-3-(dimethylaminomethylene)-2-oxo-pyrrolidine-1-carboxylate was prepared III-6 from 1-Boc-pyrrolidin-2-one (commercially available); ¹H NMR (400 MHz, CDCl₃) 7.10 (1H, s), 3.82 (2H, t), 3.01 (6H, s), 2.88 (2H, t), 1.52 (9H, s); LCMS (Method C): 0.77 min; ES–212 (M-NMe₂+OH, hydrolysis over silica during the LC).

tert-butyl (3E)-3-(dimethylaminomethylene)-2-oxo-piperidine-1-carboxylate was prepared III-7 from 1-Boc-piperidin-2-one (commercially available); ¹H NMR (400 MHz, CDCl₃) 7.51 (1H, s), 3.62 (2H, t), 3.01 (6H, s), 2.63 (2H, m), 1.79 (2H, m), 1.52 (9H, s); LCMS (Method C): 0.85 min; ES–226 (M-NMe₂+OH, hydrolysis over silica during the LC).

tert-butyl (3E)-3-(dimethylaminomethylene)-2-oxo-5-phenyl-pyrrolidine-1-carboxylate III-8 was prepared from compound IV-2; LCMS (Method D): 0.91 min; ES+312 (M+Na+).

tert-butyl (3E)-3-(dimethylaminomethylene)-2-oxo-6-phenyl-piperidine-1-carboxylate III-9 was prepared from compound IV-3; LCMS (Method D): 1.02 min; ES+326 (M+Na+).

tert-butyl (3E)-3-(dimethylaminomethylene)-2-oxo-azepane-1-carboxylate III-10 was prepared from tert-butyl 2-oxoazepane-1-carboxylate (commercially available); LCMS (Method D): 0.81 min; ES–240 (M-NMe₂+OH, hydrolysis during the LC)

tert-butyl (3E)-3-(dimethylaminomethylene)-2-oxo-6-methyl-piperidine-1-carboxylate III-11 was prepared from compound IV-4; LCMS (Method D): 090 min; ES–240 (M-NMe₂+OH, hydrolysis during the LC)

Tert-butyl-3-(hydroxymethylene)-2-oxo-4,6a-dihydro-3aH-cyclopenta[b]pyrrole-1-carboxylate II-1

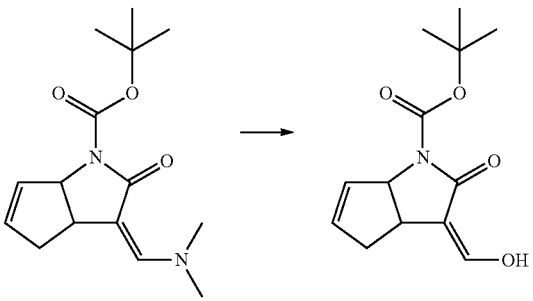 [SMILES: CN(C)/C=C1\C(=O)N(C(=O)OC(C)(C)C)C2C=CCC12 ; CC(C)(C)OC(=O)N1C(=O)/C(=C\O)C2CC=CC21]

A solution of tert-butyl-3-(dimethylaminomethylene)-2-oxo-4,6a-dihydro-3aH-cyclopenta[b]pyrrole-1-carboxylate III-1 (120 mg, 0.43 mmol) in dioxane (9 mL) was stirred with hydrochloric acid (2 M, 0.86 mL, 1.72 mmol) for 15 h at room temperature. The solution was diluted with ethyl acetate, washed with water and brine, dried, concentrated giving the desired compound as a colorless oil (101 mg, 93%); ¹H NMR (400 MHz, CDCl₃) 9.92 (1H, d), 7.05 (1H, d), 6.91 (1H, m), 5.71 (1H, m), 5.07 (1H, d), 3.46 (1H, dt), 2.87 (1H, dd), 2.31 (1H, m), 1.55 (9H, s). LCMS (Method A): 0.79 min; ES–250 (M–H⁺).

A similar procedure was used to the following compounds:

tert-butyl 3-(hydroxymethylene)-2-oxo-4,5,6,6a-tetrahydro-3aH-cyclopenta[b]pyrrole-1-carboxylate II-2 was prepared from tert-butyl 3-(dimethylaminomethylene)-2-oxo-4,5,6,6a-tetrahydro-3aH-cyclopenta[b]pyrrole-1-carboxylate III-2; ¹H NMR (400 MHz, CDCl₃) 9.85 (1H, d), 6.99 (1H, brs), 4.46 (1H, dt), 3.21 (1H, t), 2.98 (1H, d), 1.86 (4H, m), 1.60 (1H, m), 1.55 (9H, s). LCMS (Method A): 0.80 min; ES–252 (M–H⁺).

(3E)-3-(hydroxymethylene)-1-phenyl-pyrrolidin-2-one II-3 was obtained from (3E)-3-(dimethylaminomethylene)-1-phenyl-pyrrolidin-2-one III-3; LCMS (Method A): 0.80 min; ES–188 (M–H⁺).

(3E)-3-(hydroxymethylene)-5-methyl-1-phenyl-pyrrolidin-2-one II-4 was obtained from (3E)-3-(dimethylaminomethylene)-5-methyl-1-phenyl-pyrrolidin-2-one III-4; LCMS (Method A): 0.73 min; ES–202 (M–H⁺).

(3E)-3-(hydroxymethylene)-1-phenyl-piperidin-2-one II-5 was obtained from (3E)-3-(dimethylaminomethylene)-1-phenyl-piperidin-2-one III-5; LCMS (Method B): 0.90 min; ES–202 (M–H⁺).

tert-butyl (3E)-3-(hydroxymethylene)-2-oxo-pyrrolidine-1-carboxylate II-8 was prepared from tert-butyl 3-(dimethylaminomethylene)-2-oxo-pyrrolidine-1-carboxylate III-6; LCMS (Method C): 0.71 min; ES–212 (M–H⁺).

tert-butyl (3E)-3-(hydroxymethylene)-2-oxo-piperidine-1-carboxylate II-9 was obtained from tert-butyl 3-(dimethylaminomethylene)-2-oxo-piperidine-1-carboxylate III-7 during the purification on silica gel; ¹H NMR (400 MHz, CDCl₃) 13.18 (1H, brs), 7.10 (1H, s), 3.62 (2H, t), 2.31 (2H, m), 1.75 (2H, m), 1.52 (9H, s); LCMS (Method C): 0.85 min; ES–226 (M–H⁺).

tert-butyl (3Z)-3-(hydroxymethylene)-2-oxo-5-phenyl-pyrrolidine-1-carboxylate II-10 was prepared from compound III-8; LCMS (Method D): 0.91 min; ES+312 (M+Na⁺).

tert-butyl 3-(hydroxymethylene)-2-oxo-6-phenyl-piperidine-1-carboxylate II-12 was prepared from compound III-9; LCMS (Method D): 1.02 min; ES+326 (M+Na⁺).

tert-butyl (3E)-3-(hydroxymethylene)-2-oxo-azepane-1-carboxylate II-13 was prepared from compound III-10; LCMS (Method D): 0.87 min; ES–240 (M+H⁺).

tert-butyl 3-(hydroxymethylene)-2-oxo-6-methyl-piperidine-1-carboxylate II-14 was prepared from compound III-11; LCMS (Method D): 0.90 min; ES–240 (M–H⁺).

tert-butyl (3Z)-3-(hydroxymethylene)-5-methyl-2-oxo-pyrrolidine-1-carboxylate II-6

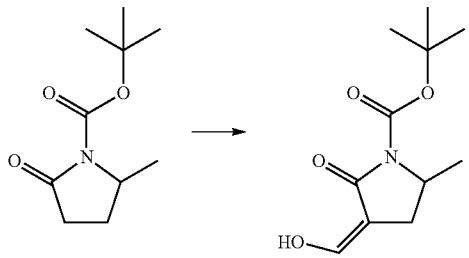 [SMILES: CC1CCC(=O)N1C(=O)OC(C)(C)C ; CC1C/C(=C/O)C(=O)N1C(=O)OC(C)(C)C]

tert-Butyl (3Z)-3-(hydroxymethylene)-5-methyl-2-oxo-pyrrolidine-1-carboxylate (as prepared in WO 2007098826) (100 mg, 0.50 mmol) in THF (1 mL) was cooled to −78° C. and potassium bis(trimethylsilyl)amide (0.5 M in toluene, 1.51 mL) was added. After 1 h, ethyl formate was added (0.081 mL, 1.0 mmol) The solution was let to warm up to 0° C. and 1N HCl was added. The solution was extracted with ethyl acetate, washed with brine, dried and concentrated to give the desired compound as colourless oil which was used without purification for the next step. LCMS (Method A) 0.73 min; ES−226 (M−H$^+$).

A similar procedure was used to prepare the following compounds:

(3E)-3-(hydroxymethylene)-1-methyl-pyrrolidine-2,5-dione II-7 was prepared from 1-methyl-pyrrolidine-2,5-dione (commercially available) using lithium bis(trimethylsilyl)amide as a base; LCMS (Method D) 0.17 min; ES−140 (M−H$^+$);

tert-butyl (3E)-3-[(4-methyl-5-oxo-2H-furan-2-yl)oxymethylene]-2-oxo-4,6a-dihydro-3aH-cyclopenta[b]pyrrole-1-carboxylate Ib-1

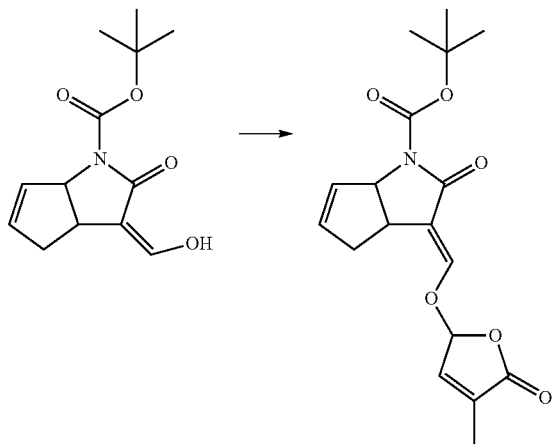 [SMILES: CC(C)(C)OC(=O)N1C(=O)/C(=C\O)C2CC=CC21 ; CC1=CC(O/C=C2/C(=O)N(C(=O)OC(C)(C)C)C3C=CCC23)OC1=O]

Method A:

To a solution of tert-butyl-3-(hydroxymethylene)-2-oxo-4,6a-dihydro-3aH-cyclopenta[b]pyrrole-1-carboxylate II-1 (100 mg, 0.39 mmol) in THF (4 mL) was added at 0° C. potassium tert-butylate (69 mg, 0.59 mmol) and 2-bromo-4-methyl-2H-furan-5-one (prepared according to Johnson & all, J. C. S. Perkin I, 1981, 1734-1743, 109 mg, 0.5969 mmol) at room temperature for 5 h. The solution was poured into water, diluted with CH$_2$Cl$_2$ and extracted 3 times. The combined organic layers were washed with brine, dried, concentrated and purified by flash chromatography (cyclohexane/ethyl acetate 2/1 then 1/1) giving the desired compound as a colorless oil (28 mg, 20%); $^1$H NMR (400 MHz, CDCl$_3$) 7.40 (1H, d), 6.91 (1H, d), 6.14 (1H, d), 5.90 (2H, m), 5.01 (1H, d), 3.50 (1H, m), 2.71 (1H, m), 2.46 (1H, m), 2.02 (3H, s), 1.55 (9H, s). LCMS (Method A): 0.90 min; ES+370 (M+Na$^+$).

A similar procedure was used to the following compounds:
tert-butyl (3E)-5-methyl-3-[(4-methyl-5-oxo-2H-furan-2-yl)oxymethylene]-2-oxo-pyrrolidine-1-carboxylate Ib-6 was prepared from tert-butyl 3-(hydroxymethylene)-5-methyl-2-oxo-pyrrolidine-1-carboxylate II-6; $^1$H NMR (400 MHz, CDCl$_3$) 7.43 (1H, m), 6.92 (1H, m), 6.13 (1H, m), 4.25 (1H, m), 2.79 (2H, m), 2.31 (1H, m), 2.27 (1H, m), 2.01 (3H, s), 1.54 (9H, s), 1.30 (3H, m); LCMS (Method A) 0.86 min; ES+669 (2M+Na$^+$).

(3E)-1-methyl-3-[(4-methyl-5-oxo-2H-furan-2-yl)oxymethylene]pyrrolidine-2,5-dione I-7 was prepared from 3-(hydroxymethylene)-1-methyl-pyrrolidine-2,5-dione II-7 (100 mg, 0.71 mmol); $^1$H NMR (400 MHz, CDCl$_3$) 7.51 (1H, s), 6.94 (1H, s), 6.18 (1H, s), 3.24 (2H, s), 3.04 (3H, s), 2.03 (3H, s); LCMS (Method B) 0.56 min; ES+260 (M+Na$^+$).

(3E)-3-[(4-methyl-5-oxo-2H-furan-2-yl)oxymethylene]-1-phenyl-pyrrolidin-2-one I-3 was prepared from 3-(hydroxymethylene)-1-phenyl-pyrrolidin-2-one II-3; $^1$H NMR (400 MHz, CDCl$_3$) 7.701 (2H, d), 7.38 (3H, m), 7.15 (1H, t), 6.94 (1H, s), 6.15 (1H, s), 3.90 (2H, m), 2.82 (2H, m), 2.03 (3H, s); LCMS (Method B) 0.88 min; ES+286, (M+H$^+$).

(3E)-5-methyl-3-[(4-methyl-5-oxo-2H-furan-2-yl)oxymethylene]-1-phenyl-pyrrolidin-2-one I-4 was prepared from 3-(hydroxymethylene)-5-methyl-1-phenyl-pyrrolidin-2-one II-4; $^1$H NMR (400 MHz, CDCl$_3$) 7.47 (5H, m), 7.21 (1H, t), 6.94 (1H, s), 6.15 (1H, s), 4.40 (1H, m), 3.08 (1H, m), 2.45 (1H, m), 2.03 (3H, s), 1.24 (3H, d); LCMS (Method C) 0.94 min; ES+300 (M+H$^+$).

(3E)-3-[(4-methyl-5-oxo-2H-furan-2-yl)oxymethylene]-1-phenyl-piperidin-2-one I-5 was prepared from 3-(hydroxymethylene)-1-phenyl-piperidin-2-one II-5: $^1$H NMR (400 MHz, CDCl$_3$) 7.51 (1H, s), 7.37 (2H, m), 7.25 (3H, m), 6.89 (1H, s), 6.15 (1H, s), 3.71 (2H, m), 2.57 (2H, m), 2.03 (5H, m); LCMS (Method C) 0.89 min; ES+300 (M+H$^+$).

tert-butyl (3E)-3-[(4-methyl-5-oxo-2H-furan-2-yl)oxymethylene]-2-oxo-azepane-1-carboxylate I-13b was prepared from tert-butyl (3E)-3-(hydroxymethylene)-2-oxo-piperidine-1-carboxylate II-13. LCMS (Method D) 0.98 min; ES+401 (M+MeCN+Na$^+$).

tert-butyl (3E)-3-[(4-methyl-5-oxo-2H-furan-2-yl)oxymethylene]-2-oxo-6-methyl-piperidine-1-carboxylate I-11b was prepared from tert-butyl (3E)-3-(hydroxymethylene)-2-oxo-piperidine-1-carboxylate II-14; LCMS (Method D) 0.97 min; ES+360 (M+Na$^+$).

tert-butyl (3E)-3-[(3,4-dimethyl-5-oxo-2H-furan-2-yl)oxymethylene]-2-oxo-4,6a-dihydro-3aH-cyclopenta[b]pyrrole-1-carboxylate Ib-19 was prepared from II-1 and 5-chloro-3,4-dimethyl-2(5H)-furanone (as prepared in *Tetrahedron* 1978, 34(13), 1935-42) by using 1,2-dimethoxyethane as the solvent; LCMS (Method D) 1.00 min; ES+262 (M-Boc+H$^+$).

tert-butyl (3E)-3-[(3,4-dimethyl-5-oxo-2H-furan-2-yl)oxymethylene]-2-oxo-4,5,6,6a-tetrahydro-3aH-cyclopenta[b]pyrrole-1-carboxylate Ib-21 was prepared from II-2 and 5-chloro-3,4-dimethyl-2(5H)-furanone (as prepared in *Tetrahedron* 1978, 34(13), 1935-42)) by using 1,2-dimethoxyethane as the solvent; LCMS (Method D) 1.03 min; ES+(no mass detected).

tert-butyl (3E)-3-[(4-methoxy-3-methyl-5-oxo-2H-furan-2-yl)oxymethylene]-2-oxo-4,6a-dihydro-3aH-cyclopenta[b]pyrrole-1-carboxylate Ib-18 was prepared from II-1 and 5-chloro-4-methoxy-3-methyl-2(5H)-furanone (as prepared in *Tetrahedron* 1978, 34(13), 1935-42 starting from 5-hydroxy-4-methoxy-3-methyl-2(5H)-furanone, *Canadian Journal of Chemistry* 1986, 64(1), 104-9) by using 1,2-dimethoxyethane as the solvent; LCMS (Method D) 0.98 min; ES+278 (M-Boc+H+).

tert-butyl (3E)-3-[(4-methoxy-3-methyl-5-oxo-2H-furan-2-yl)oxymethylene]-2-oxo-4,5,6,6a-tetrahydro-3aH-cyclopenta[b]pyrrole-1-carboxylate Ib-20 was prepared from II-2 and 5-chloro-4-methoxy-3-methyl-2(5H)-furanone (as prepared in *Tetrahedron* 1978, 34(13), 1935-42 starting from 5-hydroxy-4-methoxy-3-methyl-2(5H)-furanone, *Canadian Journal of Chemistry* 1986, 64(1), 104-9) by using 1,2-dimethoxyethane as the solvent; LCMS (Method D) 1.00 min; ES+280 (M-Boc+H+).

Method B:

To a solution of tert-butyl-3-(hydroxymethylene)-2-oxo-4,6a-dihydro-3aH-cyclopenta[b]pyrrole-1-carboxylate II-1 (1.96 g, 7.80 mmol) in THF (78 mL) was added at 0° C. potassium tert-butylate (1.35 g, 11.7 mmol) and 18-crown-6 (3.09 g, 11.7 mmol) The solution was stirred for 5 min at 0° C. and 2-chloro-4-methyl-2H-furan-5-one (prepared according to Johnson & all, J. C. S. Perkin I, 1981, 1734-1743, 109 mg, 0.5969 mmol) at 0° C. for 1 h. The solution was poured into water, diluted with ethyl acetate and extracted 3 times. The combined organic layers were washed with brine, dried, concentrated and purified by flash chromatography (cyclohexane/ethyl acetate 2/1 then 1/1) giving the desired compound as a colorless oil (2.34 g, 86%); Analytical data were identical to method A.

A similar procedure was used to the following compounds:

tert-butyl (3E)-3-[(4-methyl-5-oxo-2H-furan-2-yl)oxymethylene]-2-oxo-4,5,6,6a-tetrahydro-3aH-cyclopenta[b]pyrrole-1-carboxylate Ib-2 was prepared from tert-butyl 3-(hydroxymethylene)-2-oxo-4,5,6,6a-tetrahydro-3aH-cyclopenta[b]pyrrole-1-carboxylate II-2; $^1$H NMR (400 MHz, CDCl$_3$) 7.89 (1H, t), 6.92 (1H, m), 6.12 (1H, d), 4.40 (1H, t), 3.24 (1H, m), 2.02 (3H, s), 1.94-1.67 (6H, m), 1.52 (9H, s). LCMS (Method A): 0.92 min; ES+372 (M+Na+).

tert-butyl (3E)-3-[(4-methyl-5-oxo-2H-furan-2-yl)oxymethylene]-2-oxo-pyrrolidine-1-carboxylate I-8b was prepared tert-butyl (3E)-3-(hydroxymethylene)-2-oxo-pyrrolidine-1-carboxylate II-8: $^1$H NMR (400 MHz, CDCl$_3$)) 7.55 (1H, s), 6.89 (1H, s), 6.10 (1H, s), 3.68 (2H, m), 2.42 (2H, m), 2.01 (3H, s), 1.85 (2H, m), 1.52 (9H, s); LCMS (Method C) 0.88 min; ES+641 (2M+Na+).

tert-butyl (3E)-3-[(4-methyl-5-oxo-2H-furan-2-yl)oxymethylene]-2-oxo-piperidine-1-carboxylate I-9b was prepared from tert-butyl (3E)-3-(hydroxymethylene)-2-oxo-piperidine-1-carboxylate II-9: $^1$H NMR (400 MHz, CDCl$_3$)) 7.55 (1H, s), 6.89 (1H, s), 6.10 (1H, s), 3.68 (2H, m), 2.42 (2H, m), 2.01 (3H, s), 1.85 (2H, m), 1.52 (9H, s); LCMS (Method C) 0.93 min; ES+346 (M+Na+).

tert-butyl (3E)-3-[(4-methyl-5-oxo-2H-furan-2-yl)oxymethylene]-2-oxo-5-phenyl-pyrrolidine-1-carboxylate I-10b was prepared from tert-butyl (3E)-3-(hydroxymethylene)-2-oxo-piperidine-1-carboxylate II-10. LCMS (Method D) 1.02 min; ES+793 (2M+Na+).

tert-butyl (3E)-3-[(4-methyl-5-oxo-2H-furan-2-yl)oxymethylene]-2-oxo-6-phenyl-piperidine-1-carboxylate I-12b was prepared from tert-butyl (3E)-3-(hydroxymethylene)-2-oxo-piperidine-1-carboxylate II-12. LCMS (Method D) 1.06 min; ES+821(2M+Na+).

(3E)-3-[(4-methyl-5-oxo-2H-furan-2-yl)oxymethylene]-1,3a,4,6a-tetrahydrocyclopenta[b]pyrrol-2-one Ia-1

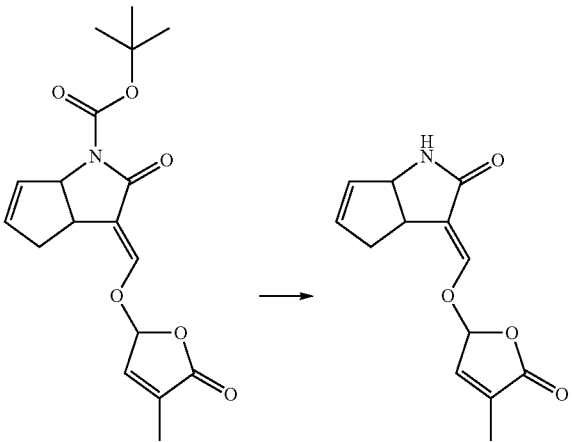 [SMILES: CC1=CC(O/C=C2/C(=O)N(C(=O)OC(C)(C)C)C3C=CCC23)OC1=O ; CC1=CC(O/C=C2/C(=O)NC3C=CCC23)OC1=O]

A solution of tert-butyl (3E)-3-[(4-methyl-5-oxo-2H-furan-2-yl)oxymethylene]-2-oxo-4,6a-dihydro-3aH-cyclopenta[b]pyrrole-1-carboxylate Ib-1 (28 mg, 0.080 mmol) in acetonitrile (1 mL) was stirred with magnesium chloride (23 mg, 0.24 mmol) at 40° C. for 7 h. The solution was then diluted into CH$_2$Cl$_2$, filtrated, concentrated and purified by flash chromatography (EtOAc, then 5% MeOH in CH$_2$Cl$_2$) giving the desired compound as a colorless oil (8 mg, 40%); $^1$H NMR (400 MHz, CDCl$_3$) 7.27 (1H, s), 6.93 (1H, s), 6.54 (1H, brs), 6.14 (1H, s), 5.87 (1H, d), 5.71 (1H, brs), 4.65 (1H, d), 3.66 (1H, m), 2.83 (1H, m), 2.46 (1H, d), 2.02 (3H, s): LCMS (Method A): 0.63 min; ES+270 (M+Na+).

A similar procedure was used to the following compounds:

(3E)-3-[(4-methyl-5-oxo-2H-furan-2-yl)oxymethylene]-1,3a,4,5,6,6a-hexahydrocyclopenta[b]pyrrol-2-one Ia-2 was prepared from tert-butyl (3E)-3-[(4-methyl-5-oxo-2H-furan-2-yl)oxymethylene]-2-oxo-4,5,6,6a-tetrahydro-3aH-cyclopenta[b]pyrrole-1-carboxylate Ib-2; $^1$H NMR (400 MHz, CDCl$_3$) 7.20 (1H, s), 6.89 (1H, s), 6.10 (1H, s), 5.54 (1H, brs), 4.07 (1H, m), 3.42 (1H, m), 2.01 (3H, s), 1.77 (2H, m), 1.65 (2H, m), 1.61 (2H, m); LCMS (Method A): 0.65 min; ES+250 (M+H+).

(3E)-3-[(4-methyl-5-oxo-2H-furan-2-yl)oxymethylene] pyrrolidin-2-one Ia-8 was prepared from Ib-8; $^1$H NMR (400 MHz, CDCl$_3$) 7.27 (1H, s), 6.95 (1H, s), 6.10 (1H, s), 3.48 (2H, t), 2.46 (2H, m), 2.01 (3H, s); LCMS (Method D): 0.51 min; ES+210 (M+H+).

(3E)-3-[(4-methyl-5-oxo-2H-furan-2-yl)oxymethylene] piperidin-2-one Ia-9 was prepared from Ib-9; $^1$H NMR (400 MHz, CDCl$_3$) 7.49 (1H, s), 7.05 (1H, brs), 6.95 (1H, s), 6.10 (1 (H, s), 3.28 (2H, t), 2.46 (2H, m), 2.01 (3H, s), 1.78 (2s, m); LCMS (Method D): 0.61 min; ES+224 (M+H+).

(3E)-3-[(4-methyl-5-oxo-2H-furan-2-yl)oxymethylene]-5-phenyl-pyrrolidin-2-one Ia-10 was prepared from Ib-10. LCMS (Method D): 0.79 min; ES+286 (M+H+).

(3E)-3-[(4-methyl-5-oxo-2H-furan-2-yl)oxymethylene]-6-phenyl-piperidin-2-one Ia-12 was prepared from Ib-12. LCMS (Method D): 0.85 min; ES+300 (M+H+).

(3E)-3-[(4-methyl-5-oxo-2H-furan-2-yl)oxymethylene]azepan-2-one Ia-13

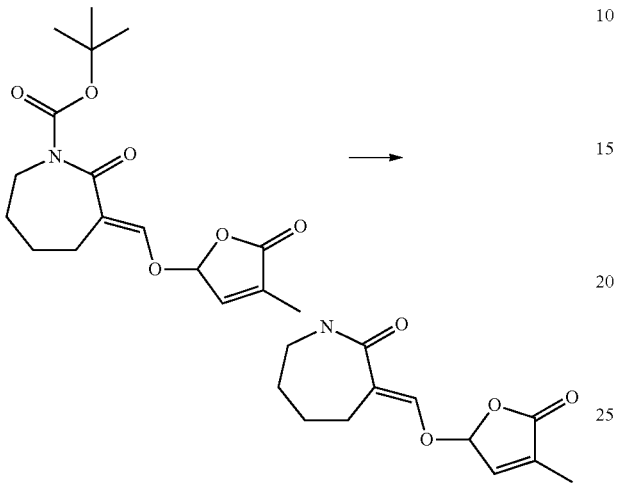

Tert-butyl (3E)-3-[(4-methyl-5-oxo-2H-furan-2-yl)oxymethylene]-2-oxo-azepane-1-carboxylate I-13b (0.55 g) was solved in dichloromethane (20 mL) and hydrogen chloride (2.0378 mL, 4M in dioxane) was added dropwise. After 30 min., dichloromethane was added and the reaction mixture was washed with sat. NaHCO$_3$. The aqueous layer was extracted once with dichloromethane, the organic layers were combined, dried over Na$_2$SO$_4$ and the solvent was evaporated to give the crude as a yellow solid. The residue was triturated in tertbutylmethylether and the solid was filtered and dried to give (3E)-3-[(4-methyl-5-oxo-2H-furan-2-yl)oxymethylene]azepan-2-one Ia-13 (0.245 g, 63%) as a white solid. LCMS (Method D): 0.67 min; ES+238 (M+H+).

A similar procedure was used to the following compounds:
(3E,3aR,6aR)-3-[(3-methoxy-4-methyl-5-oxo-2H-furan-2-yl)oxymethylene]-1,3a,4,6a-tetrahydrocyclopenta[b]pyrrol-2-one Ia-18 was prepared from tert-butyl (3E,3aR,6aR)-3-[(3-methoxy-4-methyl-5-oxo-2H-furan-2-yl)oxymethylene]-2-oxo-4,6a-dihydro-3aH-cyclopenta[b]pyrrole-1-carboxylate Ib-18 after purification using flash chromatography (CH$_2$Cl$_2$/MeOH, gradient); $^1$H NMR (400 MHz, CDCl$_3$) 7.20 (1H, dd), 6.83 (1H, bs), 5.91 (1H, d), 5.86 (1H, m), 5.71 (1H, m), 4.65 (1H, d), 4.09 (3H, d), 3.69 (1H, m), 2.85 (1H, m), 2.47 (1H, m), 1.95 (3H, d); LCMS (Method D): 0.71 min; ES+278 (M+H+).

(3E,3aR,6aR)-3-[(3,4-dimethyl-5-oxo-2H-furan-2-yl)oxymethylene]-1,3a,4,6a-tetrahydrocyclopenta[b]pyrrol-2-one Ia-19 was prepared from tert-butyl (3E,3aR,6aR)-3-[(3,4-dimethyl-5-oxo-2H-furan-2-yl)oxymethylene]-2-oxo-4,6a-dihydro-3aH-cyclopenta[b]pyrrole-1-carboxylate Ib-19 after purification using flash chromatography (CH$_2$Cl$_2$/MeOH, gradient); $^1$H NMR (400 MHz, CDCl$_3$) 7.22 (1H, dd), 6.74 (1H, bs), 5.91 (1H, bs), 5.86 (1H, m), 5.71 (1H, m), 4.64 (1H, d), 3.68 (1H, m), 2.83 (1H, m), 2.47 (1H, m), 2.01 (3H, bs), 1.89 (3H, m); LCMS (Method D): 0.73 min; ES+262 (M+0.

(3E,3aR,6aR)-3-[(3-methoxy-4-methyl-5-oxo-2H-furan-2-yl)oxymethylene]-1,3a,4,5,6,6a-hexahydrocyclopenta[b]pyrrol-2-one Ia-20 was prepared from tert-butyl (3E,3aR,6aR)-3-[(3-methoxy-4-methyl-5-oxo-2H-furan-2-yl)oxymethylene]-2-oxo-4,5,6,6a-tetrahydro-3aH-cyclopenta[b]pyrrole-1-carboxylate Ib-20 after purification using flash chromatography (CH$_2$Cl$_2$/MeOH, gradient); $^1$H NMR (400 MHz, CDCl$_3$) 7.10 (1H, dd), 6.20 (1H, bs), 5.91 (1H, d), 4.09 (3H, d), 3.45 (1H, m), 1.95 (3H, d), 1.85-1.55 (7H, m); LCMS (Method D): 0.74 min; ES+280 (M+H+).

(3E,3aR,6aR)-3-[(3,4-dimethyl-5-oxo-2H-furan-2-yl)oxymethylene]-1,3a,4,5,6,6a-hexahydrocyclopenta[b]pyrrol-2-one Ia-21 was prepared from tert-butyl (3E,3aR,6aR)-3-[(3,4-dimethyl-5-oxo-2H-furan-2-yl)oxymethylene]-2-oxo-4,5,6,6a-tetrahydro-3aH-cyclopenta[b]pyrrole-1-carboxylate Ib-21 after purification using flash chromatography (CH$_2$Cl$_2$/MeOH, gradient); $^1$H NMR (400 MHz, CDCl$_3$) 7.17 (1H, dd), 6.46 (1H, bs), 5.90 (1H, bs), 4.09 (1H, m), 3.43 (1H, m), 2.00 (3H, m), 1.88 (3H, m), 1.88-1.55 (6H, m); LCMS (Method D): 0.76 min; ES+264 (M+H+).

(3E)-1-methyl-3-[(4-methyl-5-oxo-2H-furan-2-yl)oxymethylene]-4,5,6,6a-tetrahydro-3aH-cyclopenta[b]pyrrol-2-one Ic-2

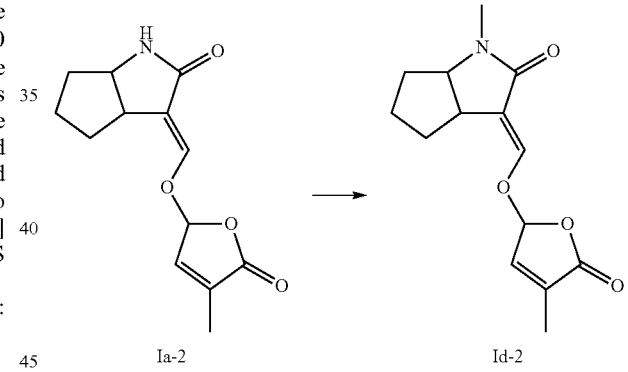

Ia-2          Id-2

(3E)-3-[(4-methyl-5-oxo-2H-furan-2-yl)oxymethylene]-1,3a,4,5,6,6a-hexahydrocyclopenta[b]pyrrol-2-one Ia-2 (104 mg) was dissolved in DMF (4 mL) and silver oxide (0.195 g) was added followed by iodomethane (0.262 mL, 0.598 g). The solution was stirred overnight at 40° C. The reaction mixture was diluted with water and extracted 3 times with ethyl acetate. The organic layers were combined, washed twice with water, once with brine, dried over Na$_2$SO$_4$ and the solvent was evaporated to give the crude (154 mg) as a brown oil. After purification by flash chromatography, (3E)-1-methyl-3-[(4-methyl-5-oxo-2H-furan-2-yl)oxymethylene]-4,5,6,6a-tetrahydro-3aH-cyclopenta[b]pyrrol-2-one Ic-2 was obtained as an oil (23 mg, 21%); LCMS (Method D): 0.78 min; ES+264 (M+H+).

A similar procedure was used to the following compounds:
(3E)-1-methyl-3-[(4-methyl-5-oxo-2H-furan-2-yl)oxymethylene]-4,6a-dihydro-3 aH-cyclopenta[b]pyrrol-2-one Ic-1; LCMS (Method D): 0.75 min; ES+262 (M+H+).

(3E)-1-acetyl-3-[(4-methyl-5-oxo-2H-furan-2-yl)oxymethylene]-4,5,6,6a-tetrahydro-3aH-cyclopenta[b]pyrrol-2-one Id-2

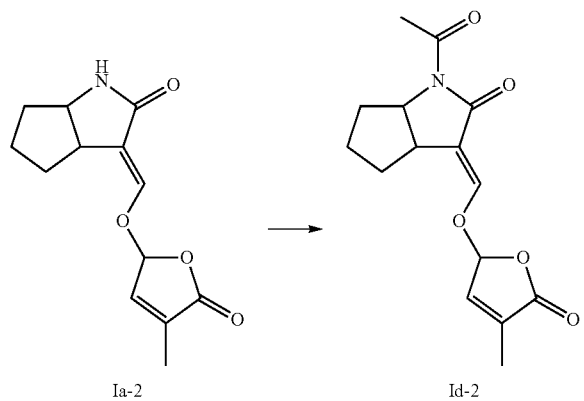 [SMILES: CC1=CC(O/C=C2/C(=O)NC3CCCC23)OC1=O ; CC(=O)N1C(=O)/C(=C/OC2C=C(C)C(=O)O2)C2CCCC21]

(3E)-3-[(4-methyl-5-oxo-2H-furan-2-yl)oxymethylene]-1,3a,4,5,6,6a-hexahydrocyclopenta[b]pyrrol-2-one Ia-2 (0.050 g) was solved in dichloromethane (2 mL) and dimethylaminopyridine (5.0 mg), triethylamine (0.113 mL, 0.082 g) and acetic anhydride (0.058 mL, 0.063 g) were mixed and stirred overnight. Triethylamine (0.113 mL, 0.082 g) and acetic anhydride (0.058 mL, 0.063 g) were added again and the reaction mixture was stirred at 40° C. for 3 h. The reaction mixture was adsorbed on isolute and purified by flash chromatography to give (3E)-1-acetyl-3-[(4-methyl-5-oxo-2H-furan-2-yl)oxymethylene]-4,5,6,6a-tetrahydro-3aH-cyclopenta[b]pyrrol-2-one Id-2 (0.054 g, 92. %); LCMS (Method D): 0.84 min; ES+292 (M+H$^+$).

A similar procedure was used to the following compounds:
(3E)-1-acetyl-3-[(4-methyl-5-oxo-2H-furan-2-yl)oxymethylene]azepan-2-one Id-13 was prepared from Ia-13; LCMS (Method D): 0.81 min; ES+280 (M+H$^+$).

(3E)-3-[(4-methyl-5-oxo-2H-furan-2-yl)oxymethylene]-1-phenyl-azepan-2-one Ic-13

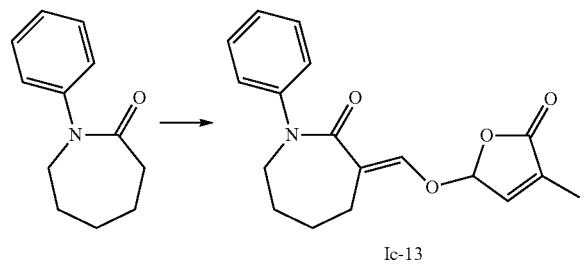 [SMILES: O=C1CCCCCN1c1ccccc1 ; CC1=CC(O/C=C2\CCCCN(c3ccccc3)C2=O)OC1=O]

1-Phenylazepan-2-one (0.500 g, as prepared in Organic Letters 2000, pages 1101-1104) was dissolved in tetrahydrofuran (30 mL) and cooled to −78° C. To the solution was added LDA (2.0 mol/L in THF/heptane/ethylbenzene, 2.6 mL) dropwise. After stirring for 10 min between −55 and −50° C., the reaction mixture was warmed up to −40° C., stirred for 5 min and ethylformate (0.657 mL, 0.605 g) was added slowly. The mixture was warmed up to 0° C. and stirred for another 30 min. 2-Chloro-4-methyl-2H-furan-5-one (0.420 g in 2 mL of THF) was added dropwise. The reaction mixture was warmed up to room temperature and stirred for 3 h. Water and ethyl acetate were added and the layers were separated. The aqueous layer was extracted with ethyl acetate, the organic layers were combined, washed with water and brine, dried over Na$_2$SO$_4$ and the solvent was evaporated to give a brown residue which was purified by flash chromatography (0-100% ethyl acetate in cyclohexane). (3E)-3-[(4-methyl-5-oxo-2H-furan-2-yl)oxymethylene]-1-phenyl-azepan-2-one Ic-13 (0.103 g, 11%) was obtained as a white solid; mp: 150-160° C.; LCMS (Method D): 0.91 min; ES+314 (M+H$^+$).

(3E,3aR,4R,6aR)-4-hydroxy-3-[[(2S)-4-methyl-5-oxo-2H-furan-2-yl]oxymethylene]-1,3a,4,6a-tetrahydrocyclopenta[b]pyrrol-2-one Ia-14″

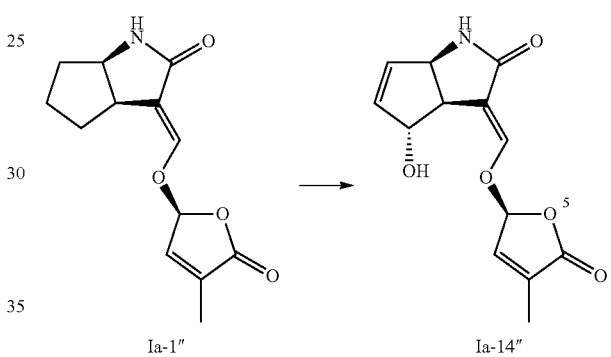

To a solution of (3E,3aR,6aR)-3-[[(2S)-4-methyl-5-oxo-2H-furan-2-yl]oxymethylene]-1,3a,4,6a-tetrahydrocyclopenta[b]pyrrol-2-one Ia-1″ (125 mg, 0.50 mmol) in 1,4-dioxane (2.5 mL) was added SeO$_2$ (67.1 mg, 0.60 mmol) The suspension was stirred at 100° C. for 4 h then the dark suspension was then allowed to cool to room temperature followed by filtration and concentration under reduced pressure. Purification using flash chromatography (CH$_2$Cl$_2$/MeOH, gradient) afforded the desired compound as a dark oil (58 mg, 44%); $^1$H NMR (400 MHz, MeOH-d$_4$) 7.35 (1H, d), 7.16 (1H, m), 6.38 (1H, m), 5.95 (1H, dd), 5.91 (1H, m), 4.76 (1H, m), 4.72 (1H, m), 3.39 (1H, m), 1.97 (3H, m): LCMS (Method D): 0.24 min; ES+264 (M+H$^+$).

A similar procedure was used to the following compounds:
(3E,3aR,4R,6aR)-4-hydroxy-3-[[(2R)-4-methyl-5-oxo-2H-furan-2-yl]oxymethylene]-1,3a,4,6a-tetrahydrocyclopenta[b]pyrrol-2-one Ia-14′ was prepared from (3E,3aR,6aR)-3-[[(2R)-4-methyl-5-oxo-2H-furan-2-yl]oxymethylene]-1,3a,4,6a tetrahydrocyclopenta[b]pyrrol-2-one Ia-1′ (103 mg, 0.42 mmol) in the presence of 2,6-lutidine (1 equiv.) under otherwise identical conditions in 16 mg (16%); $^1$H NMR (400 MHz, MeOH-d$_4$) 7.35 (1H, m), 7.17 (1H, m), 6.38 (1H, m), 5.95 (1H, m), 5.92 (1H, m), 4.77 (1H, m), 4.72 (1H, m), 3.39 (1H, m), 3.31 (1H, m), 1.96 (3H, m): LCMS (Method D): 0.24 min; ES+264 (M+H$^+$).

(3E,3aR,6aS)-5,6-dihydroxy-3-[[(2R)-4-methyl-5-oxo-2H-furan-2-yl]oxymethylene]-1,3a,4,5,6,6a-hexahydrocyclopenta[b]pyrrol-2-one Ia-15'

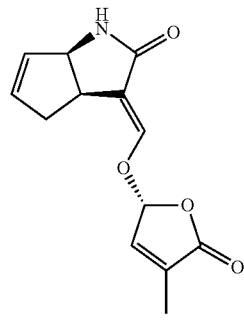

Ia-1'

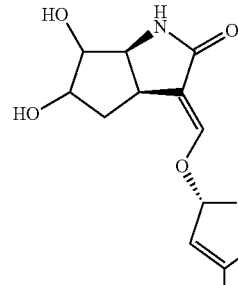

Ia-15'

To a solution of (3E,3aR,6aR)-3-[[(2R)-4-methyl-5-oxo-2H-furan-2-yl]oxymethylene]-1,3a,4,6a-tetrahydrocyclopenta[b]pyrrol-2-one Ia-1' (137 mg, 0.55 mmol) in tBuOH (3 mL) was added NMO (77.9 mg, 0.67 mmol) and acetone (0.5 mL) followed by OsO₄ (2.5-wt % in tBuOH, 560 mg, 0.055 mmol) and water (15 mg, 0.84 mmol). After 1 h at room temperature, H₂Cl₂ was added then the crude mixture was dried over Na₂SO₄, filtered and concentrated under reduced pressure. Purification using flash chromatography (CH₂Cl₂/MeOH, gradient) afforded the desired compound as a yellow foam (59 mg, 38%); ¹H NMR (400 MHz, MeOH-d₄) 7.25 (1H, d), 7.14 (1H, m), 6.34 (1H, m), 4.02 (1H, m), 3.84 (1H, dd), 3.76 (1H, dd), 3.55 (1H, m), 2.15 (1H, dt), 1.96 (3H, dd), 1.86 (1H, ddd): LCMS (Method D): 0.24 min; ES+282 (M+H⁺).

A similar procedure was used to the following compounds:
(3E,3aR,6aS)-5,6-dihydroxy-3-[[(2S)-4-methyl-5-oxo-2H-furan-2-yl]oxymethylene]-1,3a,4,5,6,6a-hexahydrocyclopenta[b]pyrrol-2-one Ia-15" was prepared from (3E,3aR,6aR)-3-[[(2S)-4-methyl-5-oxo-2H-furan-2-yl]oxymethylene]-1,3a,4,6a tetrahydrocyclopenta[b]pyrrol-2-one Ia-1"; ¹H NMR (400 MHz, MeOH-d₄) 7.25 (1H, d), 7.14 (1H, m), 6.32 (1H, m), 4.01 (1H, m), 3.84 (1H, dd), 3.76 (1H, dd), 3.55 (1H, m), 2.12 (1H, dt), 1.96 (3H, dd), 1.80 (1H, ddd): LCMS (Method D): 0.24 min; ES+282 (M+H⁺).

(3E,3aR,6aS)-5,6-dihydroxy-3-[[4-methyl-5-oxo-2H-furan-2-yl]oxymethylene]-1,3a,4,5,6,6a-hexahydrocyclopenta[b]pyrrol-2-one Ia-15 was prepared from (3E,3aR,6aR)-3-[[(4-methyl-5-oxo-2H-furan-2-yl]oxymethylene]-1,3a,4,6a tetrahydrocyclopenta[b]pyrrol-2-one Ia-1; ¹H NMR (400 MHz, MeOH-d₄) 7.25 (1H, m), 7.14 (1H, m), 6.34 (0.5H, m), 6.32 (0.5H, m), 4.02 (1H, m), 3.84 (1H, m), 3.76 (1H, m), 3.55 (1H, m), 2.13 (1H, dt), 1.96 (3H, m), 1.84 (1H, m): LCMS (Method D): 0.24 min; ES+282 (M+H⁺).

[(3E,3aR,6aS)-6-acetoxy-3-[[(2R)-4-methyl-5-oxo-2H-furan-2-0yl]oxymethylene]-2-oxo-1,3a,4,5,6,6a-hexahydrocyclopenta[b]pyrrol-5-yl]acetate Ia-16'

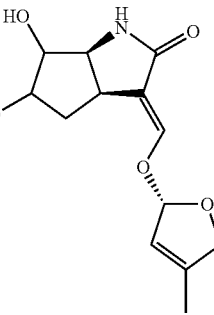

Ia-15'

Ia-16'

To a solution of (3E,3aR,6aS)-5,6-dihydroxy-3-[[(2R)-4-methyl-5-oxo-2H-furan-2-yl]oxymethylene]-1,3a,4,5,6,6a-hexahydrocyclopenta[b]pyrrol-2-one Ia-15' (25 mg, 0.09 mmol) in CH₂Cl₂ (3 mL) was added sequentially pyridine (0.015 mL, 0.178 mmol), DMAP (5.5 mg, 0.045 mmol) and Ac₂O (0.017 mL, 0.178 mmol) at room temperature under an atmosphere of argon. After 12 h, CH₂Cl₂ was added and the phases were separated followed by extraction of the aqueous phase with CH₂Cl₂. The combined organic phases were dried over Na₂SO₄, filtered and concentrated under reduced pressure. Purification using flash chromatography (CH₂Cl₂/MeOH, gradient) afforded the desired compound as a colorless solid (13.1 mg, 40%); ¹H NMR (400 MHz, CDCl₃) 7.28 (1H, d), 6.91 (1H, m), 6.53 (1H, bs), 6.12 (1H, m), 5.32 (1H, dd), 4.84 (1H, t), 3.95 (1H, dd), 3.70 (1H, m), 2.34 (1H, m), 2.10 (3H, s), 2.07 (3H, s), 2.01 (3H, m), 1.92 (1H, m): LCMS (Method D): 0.71 min; ES+366 (M+H⁺).

A similar procedure was used to the following compound:
[(3E,3aR,4R,6aR)-3-[[(2S)-4-methyl-5-oxo-2H-furan-2-yl]oxymethylene]-2-oxo-1,3a,4,6a-tetrahydrocyclopenta[b]pyrrol-4-yl]acetate Ia-17" was prepared from (3E,3aR,4R,6aR)-4-hydroxy-3-[[(2S)-4-methyl-5-oxo-2H-furan-2-yl]oxymethylene]-1,3a,4,6a-tetrahydrocyclopenta[b]pyrrol-2-one Ia-14"; ¹H NMR (400 MHz, CDCl₃) 7.30 (1H, d), 6.93 (1H, m), 6.15 (1H, m), 6.08 (1H, bs), 6.05 (1H, m), 5.95 (1H, m), 5.80 (1H, bs), 4.80 (1H, d), 3.58 (1H, m), 2.10 (3H, s), 2.05 (3H, m): LCMS (Method D): 0.63 min; ES+306 (M+H⁺).

TABLE 3

Compounds of Formula (I) (R7 = R8 = H, R6 = Me, W = O)

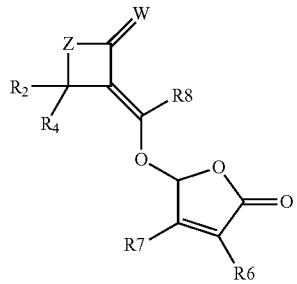

(I)

| Example | Z | R1 | R3 | R5 | R2 | R4 | LCMS method | Retention (min.) | Mass |
|---|---|---|---|---|---|---|---|---|---|
| Ib-1 | C(R3—R5)N—R1 | Boc | H | CH=CH—CH$_2$ | H | H | A | 0.90 | 370, M + Na$^+$ |
| Ia-1 | C(R3—R5)N—R1 | H | H | CH=CH—CH$_2$ | H | H | A | 0.63 | 270, M + Na$^+$ |
| Ic-1 | C(R3—R5)N—R1 | Me | H | CH=CH—CH$_2$ | H | H | D | 0.75 | 262, M + H$^+$ |
| Ib-2 | C(R3—R5)N—R1 | Boc | H | CH$_2$—CH$_2$—CH$_2$ | H | H | A | 0.92 | 372, M + Na$^+$ |
| Ia-2 | C(R3—R5)N—R1 | H | H | CH$_2$—CH$_2$—CH$_2$ | H | H | A | 0.65 | 250, M + H$^+$ |
| I-3 | C(R3—R5)N—R1 | Ph | H | H | H | H | B | 0.88 | 286, M + H$^+$ |
| I-4 | C(R3—R5)N—R1 | Ph | H | Me | H | H | C | 0.94 | 300, M + H$^+$ |
| I-5 | CH$_2$C(R3R5)N—R1 | Ph | H | H | H | H | C | 0.89 | 300, M + H$^+$ |
| Ib-6 | C(R3—R5)N—R1 | Boc | H | Me | H | H | A | 0.86 | 669, 2M + Na$^+$ |
| I-7 | C(R3—R5)N—R1 | Me | | O | H | H | D | 0.56 | 260, M + Na$^+$ |
| Ia-8 | C(R3—R5)N—R1 | H | H | H | H | H | D | 0.51 | 210, M + H$^+$ |
| Ib-8 | C(R3—R5)N—R1 | Boc | H | H | H | H | C | 0.88 | 641, 2M + Na$^+$ |
| Ia-9 | CH$_2$C(R3R5)N—R1 | H | H | H | H | H | D | 0.61 | 224, M + H$^+$ |
| Ib-9 | CH$_2$C(R3R5)N—R1 | Boc | H | H | H | H | C | 0.93 | 346, M + Na$^+$ |
| Ib-11 | CH$_2$C(R3—R5)N—R1 | Boc | Me | H | H | H | D | 0.97 | 360, M + Na$^+$ |
| Ia-11 | CH$_2$C(R3—R5)N—R1 | H | Me | H | H | H | D | 0.70 | 238, M + H$^+$ |
| Ia-12 | CH$_2$C(R3—R5)N—R1 | H | Ph | H | H | H | D | 0.85 | 300, M + H$^+$ |
| Ib-13 | CH$_2$CH$_2$C(R3—R5)N—R1 | Boc | H | H | H | H | D | 0.98 | 401, M + MeCN + Na+ |
| Id-13 | CH$_2$CH$_2$C(R3—R5)N—R1 | Ac | H | H | H | H | D | 0.81 | 280, M + H$^+$ |
| Ic-13 | CH$_2$CH$_2$C(R3—R5)N—R1 | Ph | H | H | H | H | D | 0.91 | 314, M + H$^+$ |
| Ia-13 | CH$_2$CH$_2$C(R3—R5)N—R1 | H | H | H | H | H | D | 0.67 | 238, M + H$^+$ |
| Ic-2 | C(R3—R5)N—R1 | Me | H | CH$_2$—CH$_2$—CH$_2$ | H | H | D | 0.78 | 264, M + H$^+$ |
| Id-2 | C(R3—R5)N—R1 | Ac | H | CH$_2$—CH$_2$—CH$_2$ | H | H | D | 0.84 | 292, M + H$^+$ |
| Ia-14 | C(R3—R5)N—R1 | H | H | CH=CH—CHOH | H | H | D | 0.24 | 264, M + H$^+$ |
| Ia-15 | C(R3—R5)N—R1 | H | H | (CH(OH))$_2$—CH$_2$ | H | H | D | 0.24 | 282, M + H$^+$ |
| Ib-16 | CH((CH$_2$)$_4$)C(R3—R5)N—R1* | Boc | (CH$_2$)$_4$ | H | H | H | D | 1.09 | 400, M + H$^+$ |
| Ia-16 | CH((CH$_2$)$_4$)C(R3—R5)N—R1* | H | (CH$_2$)$_4$ | H | H | H | D | 0.82 | 278, M + H$^+$ |
| Ib-17 | CH$_2$CH$_2$C(R3—R5)N—R1 | Boc | Ph | H | H | H | D | 1.10 | 436, M + Na$^+$ |
| Ia-16 | CH$_2$CH$_2$C(R3—R5)N—R1 | H | Ph | H | H | H | D | 0.90 | 314, M + H$^+$ |

*cis ring junction

TABLE 3'

Compounds of formula I (R3, R4, R8 = H)

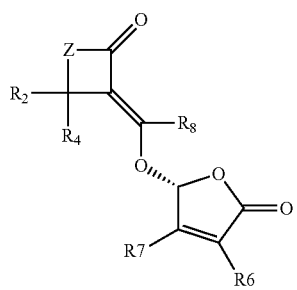

(I)

| Example | Z | R1 | R3 | R5 | R2 | R4 | LCMS method | Retention (min.) | Mass |
|---|---|---|---|---|---|---|---|---|---|
| Ia-2' | C(R3—R5)N—R1 | H | H | CH$_2$—CH$_2$—CH$_2$ | H | H | A | 0.63 | 270, M + Na$^+$ |
| Ia-1' | C(R3—R5)N—R1 | H | H | CH=CH—CH$_2$ | H | H | A | 0.63 | 270, M + Na$^+$ |
| Ib- | C(R3—R5)N—R1 | Boc | Ph | H | H | H | D | 1.02 | 793, 2M + Na$^+$ |

TABLE 3'-continued

Compounds of formula I (R3, R4, R8 = H)

$$（I）$$

| Example | Z | R1 | R3 | R5 | R2 | R4 | LCMS method | Retention (min.) | Mass |
|---|---|---|---|---|---|---|---|---|---|
| Ia-10' | C(R3—R5)N—R1 | H | Ph | H | H | H | D | 0.79 | 286, M + H⁺ |
| Ib-10' | CH₂C(R3—R5)N—R1 | Boc | Ph | H | H | H | D | 1.06 | 821, 2M + Na⁺ |
| Ia-12' | C(R3—R5)N—R1 | H | H | CH=CH—CHOH | H | H | D | 0.24 | 264, M + H⁺ |
| Ia-14' | C(R3—R5)N—R1 | H | H | CH(OH)CH(OH)—CH₂ | H | H | D | 0.24 | 282, M + H⁺ |
| Ia-15' | C(R3—R5)N—R1 | H | H | CH(OAc)CH(OAc)—CH₂ | H | H | D | 0.71 | 366, M + H⁺ |
| Ia-16' | | | | | | | | | |

TABLE 3''

Compounds of formula I (R3, R4, R8 = H)

$$（I）$$

| Example | Z | R1 | R3 | R5 | R2 | R4 | LCMS method | Retention (min.) | Mass |
|---|---|---|---|---|---|---|---|---|---|
| Ia-2'' | C(R3—R5)N—R1 | H | H | CH₂—CH₂—CH₂ | H | H | A | 0.63 | 270, M + Na⁺ |
| Ia-1'' | C(R3—R5)N—R1 | H | H | CH=CH—CH₂ | H | H | A | 0.63 | 270, M + Na⁺ |
| Ia-10'' | C(R3—R5)N—R1 | H | Ph | H | H | H | D | 0.79 | 286, M + H⁺ |
| Ia-14'' | C(R3—R5)N—R1 | H | H | CH=CH—CHOH | H | H | D | 0.24 | 264, M + H⁺ |
| Ia-15'' | C(R3—R5)N—R1 | H | H | CH(OH)CH(OH)—CH₂ | H | H | D | 0.24 | 282, M + H⁺ |
| Ia-17'' | C(R3—R5)N—R1 | H | H | CH=CH—CHOAc | H | H | D | 0.63 | 306, M + H⁺ |

TABLE 3'''

Compounds of formula I (R3, R4, R8 = H)

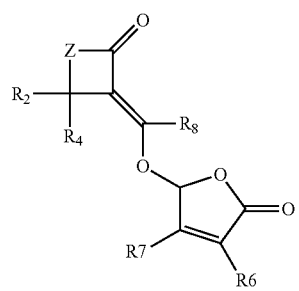

(I)

| Example | Z | R1 | R5 | R2 | R6 | R7 | LCMS method | Retention (min.) | Mass |
|---|---|---|---|---|---|---|---|---|---|
| Ib-18 | C(R3—R5)N—R1 | Boc | CH=CH—CH$_2$ | | Me | OMe | D | 0.98 | 278, M − Boc + H$^+$ |
| Ia-18 | C(R3—R5)N—R1 | H | CH=CH—CH$_2$ | | Me | OMe | D | 0.71 | 278, M + H$^+$ |
| Ib-19 | C(R3—R5)N—R1 | Boc | CH=CH—CH$_2$ | | Me | Me | D | 1.00 | 262, M − Boc + H$^+$ |
| Ia-19 | C(R3—R5)N—R1 | H | CH=CH—CH$_2$ | | Me | Me | D | 0.73 | 262, M + H$^+$ |
| Ib-20 | C(R3—R5)N—R1 | Boc | CH$_2$—CH$_2$—CH$_2$ | | Me | OMe | D | 1.00 | 280, M − Boc + H$^+$ |
| Ia-20 | C(R3—R5)N—R1 | H | CH$_2$—CH$_2$—CH$_2$ | | Me | OMe | D | 0.74 | 280, M + H$^+$ |
| Ib-21 | C(R3—R5)N—R1 | Boc | CH$_2$—CH$_2$—CH$_2$ | | Me | Me | D | 1.03 | No mass detected |
| Ia-21 | C(R3—R5)N—R1 | H | CH$_2$—CH$_2$—CH$_2$ | | Me | Me | D | 0.76 | 264, M + H$^+$ |

TABLE 4

Compounds of Formula (II) (R8 = H, W = O)

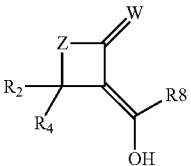

(II)

| Example | Z | R1 | R3 | R5 | R2 | R4 | LCMS method | Retention (min.) | Mass |
|---|---|---|---|---|---|---|---|---|---|
| II-1 | C(R3R5)N—R1 | Boc | H | CH=CH—CH$_2$ | H | H | A | 0.79 | 250, M − H$^+$ |
| II-2 | C(R3R5)N—R1 | Boc | H | —CH$_2$—CH$_2$—CH$_2$ | H | H | A | 0.80 | 252, M − H$^+$ |
| II-3 | C(R3R5)N—R1 | Ph | H | H | H | H | A | 0.80 | 188, M − H$^+$ |
| II-4 | C(R3R5)N—R1 | Ph | H | Me | H | H | A | 0.73 | 202, M − H$^+$ |
| II-5 | CH$_2$C(R3R5)N—R1 | Ph | H | H | H | H | B | 0.90 | 202, M − H$^+$ |
| II-6 | C(R3R5)N—R1 | Boc | H | Me | H | H | A | 0.73 | 226, M − H$^+$ |
| II-7 | C(R3R5)N—R1 | Me | | O | H | H | D | 0.17 | 140, M − H$^+$ |
| II-8 | C(R3R5)N—R1 | Boc | H | H | H | H | C | 0.71 | 212, M − H$^+$ |
| II-9 | CH$_2$C(R3R5)N—R1 | Boc | H | H | H | H | C | 0.85 | 226, M − H$^+$ |
| II-10 | C(R3—R5)N—R1 | Boc | Ph | H | H | H | D | 0.91 | 312, M + Na$^+$ |
| II-12 | CH$_2$C(R3—R5)N—R1 | Boc | Ph | H | H | H | D | 1.02 | 326, M + Na$^+$ |
| II-13 | CH$_2$CH$_2$C(R3—R5)N—R1 | Boc | H | H | H | H | D | 0.87 | 240, M − H$^+$ |
| II-14 | CH$_2$C(R3—R5)N—R1 | Boc | Me | H | H | H | D | 0.90 | 240, M − H$^+$ |
| II-15* | CH((CH$_2$)$_4$)C(R3—R5)N—R1 | Boc | (CH$_2$)$_4$ | | H | H | D | 1.03 | 280, M − H$^+$ |
| II-16 | CH$_2$CH$_2$C(R3—R5)N—R1 | Boc | Ph | H | H | H | D | 1.08 | 340, M + Na$^+$ |

*cis ring junction

TABLE 5

Compounds of Formula (III) (R8 = H, W = O)

(III)

| Example | Z | R1 | R3 | R5 | R2 | R4 | LCMS method | Retention (min.) | Mass |
|---|---|---|---|---|---|---|---|---|---|
| III-1 | C(R3R5)N—R1 | Boc | H | CH=CH—CH$_2$ | H | H | A | 0.83 | 279, M + H$^+$ |
| III-2 | C(R3R5)N—R1 | Boc | H | —CH$_2$—CH$_2$—CH$_2$ | H | H | A | 0.86 | 583, 2M + Na$^+$ |
| III-3 | C(R3R5)N—R1 | Ph | H | H | H | H | C | 0.67 | 465, 2M + Na$^+$ |
| III-4 | C(R3R5)N—R1 | Ph | H | Me | H | H | C | 0.70 | 493 (2M + Na+) |
| III-5 | CH$_2$C(R3R5)N—R1 | Ph | H | H | H | H | B | 0.70 | 204, M + H$^+$ |
| III-6* | C(R3R5)N—R1 | Boc | H | H | H | H | C | 0.71 | 212, M − NMe$_2$ + OH |
| III-7* | CH$_2$C(R3—R5)N—R1 | Boc | H | H | H | H | C | 0.85 | 226, M − NMe$_2$ + OH |
| III-8* | C(R3—R5)N—R1 | Boc | Ph | H | H | H | C | 0.71 | 212, M − NMe$_2$ + OH$^-$ |
| III-9* | CH$_2$C(R3—R5)N—R1 | Boc | Ph | H | H | H | D | 1.02 | 326, M − NMe$_2$ + OH + Na$^+$ |
| III-10* | CH$_2$CH$_2$C(R3—R5)N—R1 | Boc | H | H | H | H | D | 0.81 | 240, M − NMe$_2$ + OH |
| III-11* | CH$_2$C(R3—R5)N—R1 | Boc | Me | H | H | H | D | 0.91 | 240, M − NMe$_2$ + OH |
| III-12* | CH((CH$_2$)$_4$)C(R3—R5)N—R1** | Boc | (CH$_2$)$_4$ | H | H | H | D | 1.04 | 280, M − NMe$_2$ + OH |
| III-13* | CH$_2$CH$_2$C(R3—R5)N—R1 | Boc | Ph | H | H | H | D | 1.08 | 340, M − NMe$_2$ + OH + Na$^+$ |

*product hydrolysed during the LCMS.
**cis ring junction

TABLE 6

Compounds of Formula (IV) (W = O, Z = C(R3R5)NR1)

(IV)

| Example | Z | R1 | R3 | R5 | R2 | R4 | NMR |
|---|---|---|---|---|---|---|---|
| IV-1 | C(R3R5)N—R1 | Boc | H | CH=CH—CH$_2$ | H | H | 5.51 (2 H, m), 5.00 (1 H, d), 3.89 (1 H, m), 3.78 (1 H, dd), 3.70 (1 H, m), 2.29 (1 H, dd), 2.22 (1H, m), 1.51 (9 H, s). |
| IV-2 | C(R3—R5)N—R1 | Boc | Ph | H | H | H | LCMS (Method D): RT = 0.94 min, (325, M + MeCN + Na$^+$) |
| IV-3 | CH$_2$C(R3—R5)N—R1 | Boc | Ph | H | H | H | LCMS (Method D): RT = 0.98 min, (339, M + MeCN + Na$^+$) |
| IV-4 | CH$_2$C(R3—R5)N—R1 | Boc | Me | H | H | H | LCMS (Method D): RT = 0.86 min, (236, M + Na$^+$) |
| IV-5* | CH((CH$_2$)$_4$)C(R3—R5)N—R1 | Boc | (CH$_2$)$_4$ | H | H | H | LCMS (Method D): RT = 1.01 min, (276, M + Na$^+$) |
| IV-6 | CH$_2$CH$_2$C(R3—R5)N—R1 | Boc | Ph | H | H | H | LCMS (Method D): RT = 1.07 min, (312, M + Na$^+$) |

*cis ring junction

Biological Examples

The effect of compounds of Formula (I) on germination of *Orobanche cumana* Wallr. seeds was evaluated on glass fiber filter paper (GFFP) in petri dishes. Seeds were preconditioned at moisture and suitable temperature to become responsive to the specific chemical germination stimulants.

Test compounds were dissolved in DMSO (10 000 mg l$^{-1}$) and stored at room temperature in a desiccators with desiccants. The stock solutions were dissolved with deionised water to the appropriate final test concentration.

Seeds of *O. cumana* race 'F' (IN153) were collected from a sunflower field in Manzanilla (Seville, Spain) in 2006 and stored at room temperature. To separate seeds from heavy organic debris, a modified sucrose floatation technique as described by Hartman & Tanimonure (Plant Disease (1991), 75, p. 494) was applied. Seeds were filled into a separation funnel and stirred in water. When seeds floated to the surface, the water fraction containing heavy debris was discarded. Seeds were re-suspended in 2.5M sucrose solution (specific gravity of 1.20) and heavy debris was allowed to settle down for 60 min After removing debris, seeds were disinfected in 1% sodium hypochlorite solution and 0.025% (v/v) Tween 20 for 2 min. The seeds were decanted onto two layers of cheese-cloth, rinsed with sterile deionised water and re-suspended in sterile deionised water. Two ml of the seed suspension containing approximately 150-400 seeds were spread evenly on two layers of sterile glass fiber filter paper disc (Ø9 mm) in Petri dishes (Ø9 cm). After wetting the discs with 3 ml sterile deionised water, petri dishes were sealed with parafilm. Seeds were incubated for 10 days at 20° C. in the dark for seed conditioning. The upper disc with conditioned seeds was briefly dried, transferred to a petri dish lined with a dry GFFP disc, and wetted with 6 ml of the appropriate test solution. The compounds of Formula (I) were tested at concentrations of 0.001, 0.01, 0.1, or 1 mg l$^{-1}$. The strigolactone analogue GR24 was included as positive control and 0.01% DMSO as negative control. All treatments were tested in five replicates. Seeds were re-incubated at 20° C. in the dark and examined for germination 10 days later. The radicles of germinated seeds were stained for 5 min with blue ink (MIGROS, Switzerland) in 5% acetic acid according to Long et al. (Seed Science Research (2008), 18, p. 125). After staining, seeds were photographed using a camera stand mounted with a digital SLR camera (Canon EOS 5D). Germination of 100 seeds per replicate was evaluated on digital images. Seeds were considered germinated when the radicle protruded from the seed coat. The results of the *Orobanche* seed germination tests are shown in Tables B1 to B6.

TABLE B1

Effect of strigolactone analogs on germination of preconditioned *Orobanche cumana* seeds.

| | Concentration (mg l$^{-1}$) | | |
|---|---|---|---|
| Compound | 1 | 0.1 | 0.001 |
| | Germination (%)* | | |
| Ib-1 | 92.6 | 25.8 | 0 |
| Ia-1 | 23.2 | 24.6 | 1.4 |
| Ib-2 | 54.8 | 18.2 | 0 |
| Ib-6 | 5.6 | 1.8 | 0.4 |
| GR-24 | 80.2 | 47.2 | 24.8 |

*Mean; N = 5 × 100 seeds; Seed lot IN153 Control, DMSO 0.01% (w/w): 0.4% germination

TABLE B2

Effect of strigolactone analogs on germination of preconditioned *Orobanche cumana* seeds.

| | Concentration (mg l$^{-1}$) | | |
|---|---|---|---|
| compound | 1 | 0.1 | 0.01 |
| | Germination (%)* | | |
| I-7 | 17.2 | 1.4 | 1 |
| I-5 | 42.2 | 0 | 1 |
| Ib-8 | 1.4 | 2.8 | 0.2 |
| I-4 | 18.2 | 1 | 0.6 |
| Ia-2 | 83.4 | 65.4 | 75.4 |
| I-3 | 19.2 | 1.6 | 0 |
| GR-24 | 85.2 | 46.4 | 12.2 |

*Mean; N = 5 × 100 seeds; Seed lot IN153 Control, DMSO 0.01% (w/w): 2.4% germination

TABLE B3

Effect of strigolactone analogs on germination of preconditioned *Orobanche cumana* seeds.

| | Concentration (mg l$^{-1}$) | | |
|---|---|---|---|
| compound | 0.1 | 0.01 | 0.001 |
| | Germination (%)* | | |
| Ib-10 | 71.8 | 72.4 | 72.8 |
| Ib-12 | 90.2 | 89 | 91 |
| Ia-12 | 92.4 | 86.8 | 93.3 |
| GR-24 | 84.2 | 51 | 26 |

*Mean; N = 5 × 100 seeds; Seed lot IN153 Control, DMSO 0.01% (w/w): 0% germination

TABLE B4

Effect of strigolactone analogs on germination of preconditioned *Orobanche cumana* seeds.

| | Concentration (mg l$^{-1}$) | | |
|---|---|---|---|
| compound | 1 | 0.01 | 0.01 |
| | Germination (%)* | | |
| Ib-13 | 90.8 | 83 | 48 |
| GR-24 | 95.2 | 86.6 | 88 |

*Mean; N = 5 × 100 seeds; Seed lot IN153 Control, DMSO 0.01% (w/w): 0.75% germination

TABLE B5

Effect of strigolactone analogs on germination of preconditioned *Orobanche cumana* seeds.

| | Concentration (mg l$^{-1}$) | | |
|---|---|---|---|
| compound | 1 | 0.01 | 0.01 |
| | Germination (%)* | | |
| Ia-13 | 70 | 34.2 | 25.6 |
| GR-24 | 86.6 | 78.4 | 65 |

*Mean; N = 5 × 100 seeds; Seed lot IN153 Control, DMSO 0.01% (w/w): 1.4% germination

TABLE B6

Effect of strigolactone analogs on germination of preconditioned *Orobanche cumana* seeds.

| | Concentration (mg l$^{-1}$) | | |
|---|---|---|---|
| Compound | 1 | 0.1 | 0.001 |
| | Germination (%)* | | |
| Ia-1' | 54.8 | 55.3 | 68.0 |
| Ia-2'' | 1.8 | 0 | 0 |
| GR-24 | 58.1 | 43.2 | 23.0 |

*Mean; N = 5 × 100 seeds; Seed lot IN153 Control, DMSO 0.01% (w/w): 2.4% germination Biological Examples 2

The effect of compounds of Formula (I) on the germination of *Brassica oleracea* cv *Botrytis* or common cauliflower was tested on two types of cauliflowers: temperate types and tropical types. These two types were chosen because they display different sensitivities to the light conditions and temperature during germination. Germination of a sensitive temperate type is inhibited by light at 10° C. while for the tropical types germination at 20° is stimulated by the presence of light.

Hence, 10° C. in the light and 20° C. in the dark are considered suboptimal or stress conditions for germination of the two types, respectively.

The temperate seed batches tested are part of commercially produced seed batches of various varieties which are known to be sensitive to light at 10° C. These seeds were harvested and cleaned according standard commercial procedures. Ready seed batches were used (Ready indicates the processing level of these seeds: they have been cleaned and sized but received no other treatments). The tropical seed batches tested are part of seed batches produced as basic seed (for maintenance of the parental line) and were processed accordingly.

Germination was assessed using the standard paper germination test for Brassica: Fifty seeds were placed on blue germination paper, which was moistened with the appropriate solutions, in closed oblong germination boxes. Each condition was tested in duplo. Germination boxes were placed in controlled germination cabinets with the appropriate temperature and light conditions. Germination of seeds was counted at regular intervals. Seeds were considered to be germinated when the radical had protruded the testa and endosperm (radical size approximately 1 mm)

Test compounds were dissolved in DMSO at a concentration of 50 mM and stored at −20° C. The strigolactone analogue GR24 (commercially available as a racemic mixture of 2 diastereoisomers, referred to as "synthetic strigolactone GR-24" and first prepared by Johnson A. W. & all, Journal of the Chemical Society, Perkin Transactions 1, 1981, page 1734-1743) was included as positive control. Germination solutions were prepared by diluting the stock solutions with demineralized water till 25 μM. As control solutions demineralized water and a 0.05% v/v DMSO solution were used.

The effect of the strigolactone derivatives on germination is shown in tables 7 and 8. These results show that strigolactones stimulate germination at suboptimal conditions.

TABLE

Germination of seeds of the temperate cauliflower Spacestar (seed batch 11B313; produced in South Africa in 2010 (cold-sensitive) and seed batch 11B314; produced in Chile in 2010 (not cold sensitive)) in the presence of 25 μM of the different strigolactone derivatives at 10° C. and in the light. A: First set of Strigolactones; B: Second set of Strigolactones. Sets were tested in separate experiments and with two independent experiments for each set.

|  | Spacestar 11B313 | | Spacestar 11B314 | |
| --- | --- | --- | --- | --- |
| compound | $G_{max}{}^a$ (%) | stimulation$^b$ (%) | $G_{max}{}^a$ (%) | stimulation$^b$ (%) |
| A | | | | |
| DMSO | 60.0 | 0.0 | 90.5 | 0.0 |
| GR24 | 71.5 | 19.2 | 93.5 | 3.3 |
| Ia-1 | 72.0 | 20.0 | 96.5 | 6.6 |
| B | | | | |
| DMSO | 54.0 | 0.0 | 86.0 | 0.0 |
| GR24 | 80.0 | 48.1 | 93.0 | 8.1 |
| Ia-8 | 77.0 | 42.6 | 93.0 | 8.1 |
| Ia-13 | 42.3 | −21.8 | 92.5 | 7.6 |

$^a$total germination as percentage of sown seeds
$^b$extra germination compared to the DMSO treatment (control), expressed as percentage of the germination in the DMSO treatment

The invention claimed is:
1. A compound of Formula (I)

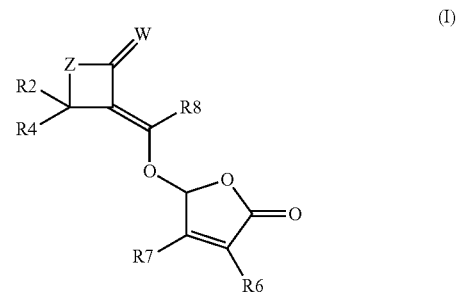

wherein
W is O or S;
Z is NR1, C(R3R5)NR1, C(R11R12)C(R3R5)NR1, (R13R14)C(R11R12)C(R3R5)NR1, provided that NR1 is always in alpha of the C=W group;
R1 is hydrogen, $C_1$-$C_6$ alkoxy, hydroxyl, amine, N—$C_1$-$C_6$ alkyl amine, N,N-di-$C_1$-$C_6$ alkyl amine, $C_1$-$C_6$ alkyl optionally substituted by one to five R10, $C_1$-$C_6$ haloalkyl, $C_1$-$C_6$ haloalkoxy, $C_1$-$C_8$ alkylcarbonyl, $C_1$-$C_8$ alkoxycarbonyl, $C_1$-$C_8$ alkylsulfonyl, $C_1$-$C_6$ alkylsulfinyl, aryl optionally substituted by one to five R10, heteroaryl optionally substituted by one to five R10, heterocyclyl optionally substituted by one to five R10, or benzyl optionally substituted by one to five R10;
R2, R3, R4, R5, R11, R12, R13 and R14 are independently selected from the group consisting of:
(i) A bond, hydrogen, halogen, hydroxyl, nitro, cyano, formyl, formyloxo, formylamino, acetyloxo, $C_1$-$C_6$ alkoxy, $C_1$-$C_6$ haloalkoxy, $C_1$-$C_6$ alkyl optionally substituted by one to five R10, $C_1$-$C_6$ alkylcarbonyl, $C_1$-$C_6$ alkoxycarbonyl, hydroxycarbonyl, aminocarbonyl, N—$C_1$-$C_6$ alkyl amine, N,N-di-$C_1$-$C_6$ alkyl amine, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, aryl optionally substituted by one to five R10, heteroaryl optionally substituted by one to five R10, vinyl optionally substituted by one to three R9, ethynyl optionally substituted by one R9, a saturated or partially unsaturated 3 to 7 membered cycloalkyl or heterocyclyl, optionally substituted by R10;
(ii) Any two of R2, R3, R4, R5, R11, R12, R13 and R14 form a saturated or partially unsaturated 3 to 7 membered cycloalkyl or heterocyclyl, optionally substituted by R9; and
(iii) R2 and R4, R3 and R5, R11 and R12 and/or R13 and R14 form an oxo group;
R6 and R7 are independently hydrogen, $C_1$-$C_3$ alkyl, hydroxyl, halogen or $C_1$-$C_3$ alkoxy;
R8 is hydrogen, $C_1$-$C_6$ alkyl optionally substituted by one to five R10, halogen, $C_1$-$C_6$ alkylthio, $C_1$-$C_6$ haloalkylthio, $C_1$-$C_6$ alkylsulfinyl, N—$C_1$-$C_6$ alkyl amine, N,N-di-$C_1$-$C_6$ alkyl amine, $C_1$-$C_6$ haloalkylsulfinyl, $C_1$-$C_6$ alkylsulfonyl, or $C_1$-$C_6$ haloalkylsulfonyl;
R9 is halogen, cyano, nitro, $C_1$-$C_6$ alkyl, $C_1$-$C_6$ haloalkoxy, $C_1$-$C_6$ alkoxy, acetyloxo, amine, N—$C_1$-$C_6$ alkyl amine, N,N-di-$C_1$-$C_6$ alkyl amine, $C_1$-$C_6$ alkyl optionally substituted by one to five R10, $C_1$-$C_6$ alkylcarbonyl, $C_1$-$C_6$ alkoxycarbonyl, aryl optionally substituted by one to five R10, $C_2$-$C_6$ alkenyl, or $C_2$-$C_6$ alkynyl, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl, or $C_1$-$C_6$ haloalkylsulfonyl;

R10 is hydroxyl, acetyloxo, cyano, nitro, halogen, $C_1$-$C_6$ alkyl, $C_1$-$C_6$ alkoxy, $C_1$-$C_6$ haloalkoxy, $C_1$-$C_6$ haloalkyl, $C_2$-$C_6$ alkenyl, or $C_2$-$C_6$ alkynyl, $C_1$-$C_6$ alkylthio, $C_1$-$C_6$ haloalkylthio, $C_1$-$C_6$ alkylsulfinyl, N—$C_1$-$C_6$ alkyl amine, N,N-di-$C_1$-$C_6$ alkyl amine, $C_1$-$C_8$ haloalkylsulfinyl, $C_1$-$C_8$ alkylsulfonyl, or $C_1$-$C_8$ haloalkylsulfonyl;
or a salt or N-oxide thereof.

2. A compound according to claim 1, wherein W is O.

3. A compound according to claim 2, wherein
Z is NR1, C(R3R5)NR1 or C(R11R12)C(R3R5)NR1;
R1 is hydrogen, $C_1$-$C_6$ alkoxy, $C_1$-$C_6$ alkyl optionally substituted by one to five R10, $C_1$-$C_8$ alkylcarbonyl, $C_1$-$C_8$ alkoxycarbonyl, aryl optionally substituted by one to five R10, heteroaryl optionally substituted by one to five R10, heterocyclyl optionally substituted by one to five R10, or benzyl optionally substituted by one to five R10;
R2, R3, R4, R5, R11, R12, R13 or R14 are independently selected from the group consisting of:
(i) A bond, hydrogen, $C_1$-$C_6$ alkoxy, $C_1$-$C_6$ alkyl, $C_1$-$C_6$ alkyl optionally substituted by one to five R10, $C_1$-$C_6$ alkoxycarbonyl, aryl optionally substituted by one to five R10, heteroaryl optionally substituted by one to five R10, or saturated or partially unsaturated 3 to 7 membered cycloalkyl or heterocyclyl optionally substituted by R10;
(ii) Any two of R2, R3, R4, R5, R11, R12, R13 and R14 can form a saturated or partially unsaturated 5 to 6 membered cycloalkyl or heterocyclyl, optionally substituted by R9; and
(iii) R2 and R4, R3 and R5, R11 and R12, and/or R13 and R14 form an oxo group;
R6 is hydrogen, methyl, or ethyl;
R7 is hydrogen, methyl, methoxy, chlorine or ethyl;
R8 is hydrogen, methyl, or ethyl; and
R10 is hydroxyl, cyano, nitro, halogen, $C_1$-$C_6$ alkyl, $C_1$-$C_6$ alkoxy, or $C_1$-$C_6$ haloalkyl.

4. A compound according to claim 3, wherein
Z is C(R3R5)NR1;
R1 is hydrogen, $C_1$-$C_6$ alkyl optionally substituted by one to five R10, $C_1$-$C_8$ alkylcarbonyl, $C_1$-$C_8$ alkoxycarbonyl, aryl optionally substituted by one to five R10, or benzyl optionally substituted by one to five R10;
R2, R3, R4, R5, R11 or R12 are independently selected from the group consisting of:
i) hydrogen, methyl, ethyl, or phenyl;
ii) R2 and R5, or R5 and R11 form a saturated or partially unsaturated 5 to 6 membered cycloalkyl; and
iii) R2 and R4 and/or R3 and R5 form an oxo group;
R6 is methyl;
R7 and R8 are hydrogen; and
R10 is cyano, nitro, chlorine, bromine, fluorine, methyl, methoxy, or trifluoromethyl.

5. A compound according to claim 1, wherein R1 is selected from the group consisting of hydrogen, methyl, ethyl, phenyl, benzyl, acetate, tert-butoxycarbonyl and methoxycarbonyl.

6. A plant growth regulator or seed germination promoting composition, comprising a compound according to claim 1, and an agriculturally acceptable formulation adjuvant.

7. A method for regulating the growth of plants at a locus, wherein the method comprises applying to the locus a plant growth regulating amount of a compound according to claim 1.

8. A method for promoting the germination of seeds comprising applying to the seeds, or a locus containing seeds, a seed germination promoting amount of a compound according to claim 1.

9. A product comprising plant seed coated with a composition comprising a compound according to Formula (I) of claim 1.

10. A method for controlling weeds comprising applying to a locus containing weed seeds a seed germination promoting amount of a compound according to claim 1, allowing the seeds to germinate, and then applying to the locus a post-emergence herbicide.

* * * * *